(12) United States Patent
Dasgupta et al.

(10) Patent No.: US 8,982,344 B2
(45) Date of Patent: Mar. 17, 2015

(54) APPARATUS AND METHODS FOR CHIRALITY DETECTION

(71) Applicant: University of Calcutta, Kolkata, West Bengal (IN)

(72) Inventors: Anjan Kr. Dasgupta, West Bengal (IN); Sarita Roy, West Bengal (IN)

(73) Assignee: University of Calcutta, Kolkata (IN)

( * ) Notice: Subject to any disclaimer, the term of this patent is extended or adjusted under 35 U.S.C. 154(b) by 0 days.

(21) Appl. No.: 14/134,899

(22) Filed: Dec. 19, 2013

(65) Prior Publication Data

US 2014/0107942 A1   Apr. 17, 2014

Related U.S. Application Data

(62) Division of application No. 13/513,068, filed as application No. PCT/IB2011/000149 on Jun. 21, 2011, now Pat. No. 8,638,434.

(30) Foreign Application Priority Data

Mar. 21, 2011 (IN) .............................. 376/KOL/2011

(51) Int. Cl.
| | | |
|---|---|---|
| *G01J 3/447* | (2006.01) | |
| *G01J 3/30* | (2006.01) | |
| *G01J 4/00* | (2006.01) | |
| *G01N 21/25* | (2006.01) | |
| *G01N 21/64* | (2006.01) | |
| *G01N 23/22* | (2006.01) | |

(52) U.S. Cl.
CPC ........ *G01N 21/6402* (2013.01); *G01N 21/6445* (2013.01); *G01N 23/22* (2013.01)
USPC ........... 356/322; 356/317; 356/318; 356/364; 356/417

(58) Field of Classification Search
None
See application file for complete search history.

(56) References Cited

U.S. PATENT DOCUMENTS

| | | | |
|---|---|---|---|
| 4,912,059 A | | 3/1990 | Newman et al. |
| 4,946,279 A | * | 8/1990 | Ohkubo ........................ 356/318 |
| 5,168,326 A | | 12/1992 | Tokieda et al. |
| 5,477,327 A | | 12/1995 | Bergman |

(Continued)

FOREIGN PATENT DOCUMENTS

| | | |
|---|---|---|
| WO | WO-01/06918 | 2/2001 |
| WO | WO-2007/002182 | 1/2007 |

OTHER PUBLICATIONS

Baev, A., et al., "A quantum chemical approach to the design of chiral negative index materials", Opt Express, vol. 15, No. 9, Apr. 2007, pp. 5730-5741.

(Continued)

*Primary Examiner* — Tarifur Chowdhury
*Assistant Examiner* — Hina F Ayub
(74) *Attorney, Agent, or Firm* — Foley & Lardner LLP

(57) ABSTRACT

Technologies are generally described for systems and methods for detecting chiral properties of materials and separating materials based on their chiral properties. A chiral vector is constructed from anisotropy properties of a polarization-dependent output signal from a sample. Different types of molecules from the sample can be differentiated based on a magnitude of the chiral vector. Chiral properties of the sample can be detected based on an angle of the chiral vector. The output signal can be a fluorescent emission from the sample and can be used to detect chiral properties of a substantially opaque sample.

17 Claims, 11 Drawing Sheets

(56) References Cited

U.S. PATENT DOCUMENTS

| | | | |
|---|---|---|---|
| 5,621,528 A | 4/1997 | Rokos | |
| 5,876,672 A * | 3/1999 | Dandliker et al. | 422/82.08 |
| 5,896,198 A | 4/1999 | Chou et al. | |
| 6,327,037 B1 | 12/2001 | Chou et al. | |
| 2005/0227366 A1 | 10/2005 | Tobe et al. | |
| 2009/0101843 A1* | 4/2009 | Henshaw et al. | 250/484.4 |
| 2009/0208548 A1* | 8/2009 | Mason et al. | 424/405 |
| 2009/0220452 A1* | 9/2009 | Botti | 424/85.2 |
| 2010/0253934 A1* | 10/2010 | D'Ascenzi et al. | 356/51 |
| 2012/0044488 A1* | 2/2012 | Senac | 356/316 |

OTHER PUBLICATIONS

Castiglioni, E., et al., "An integrating sphere to measure CD from difficult samples," Chirality, 2000, vol. 12, pp. 291-294.

Chiral Technologies, "Chiral Columns—Overview," Webpage: http://www.chiraltech.com/col_overview.asp, accessed Jan. 10, 2012, 1 page.

Conger, B.M., "Polarized Photoluminescence from Nematic and Chiral-Nematic Liquid Crystalline Films," Dissertation, University of Rochester, 1998, 219 pages.

Davies, N.M., et al., "Effect of the Enantiomers of Flurbiprofen, Ibuprofen, and Ketoprofen on Intestinal Permeability," Journal of Pharmaceutical Sciences: vol. 85, No. 11, 1996, pp. 1170-1173.

Eriksson, T., et al., "Clinical pharmacology of thalidomide," Eur J Clin Pharmacol, vol. 57, No. 5, Aug. 2001, pp. 365-376.

Guo, X., et al., "Angular Measurements of Light Scattered by Turbid Chiral Media using Linear Stokes Polarimeter," J. Biomed, Opt., vol. 11, No. 4, Jul.-Aug. 2006, pp. 041105-1 to 0041105-10.

Hassey-Paradise, R., et al., "Dissymmetries in Fluorescence Excitation and Emission from Single Chiral Molecules," Chirality, vol. 21, 2009, pp. E265-E276.

Hazen, R.M., "Chiral Selection," Carnegie Institute for Science, Webpage: http://hazen.ciw.edu/research/chiral, accessed Jan. 10, 2012, 2 pages.

International Search Report and Written Opinion received for PCT/IB2011/001409 mailed Oct. 12, 2011, pp. 1-16.

Jeong, K., et al., "Origin of self assembled helical supramolecular structures in achiral C6 Biphenyl carboxylic acid compound," Chem mater., vol. 18, 2006, pp. 680-690.

Johansson, L.B.-A et al., "Spectroscopic Studies of fluorescent perylene dyes," Spectrochimica Acta, 1991, vol. 47A, No. 7, pp. 857-861.

Kimaru, I. W., et al., 01CCharacterization of Chiral Interactions Using Fluorescence Anisotropy, Anal. Chem., vol. 78, No. 24, pp. 8485-8490, American Chemical Society (2006).

Kitaev, V., "Chiral nanoscale building blocks—from understanding to applications," J. Mater. Chem., vol. 18, 2008, pp. 4745-4749.

Kriech, M.A., et al., "Label-free chiral detection of melittin binding to a membrane," JACS, vol. 125, No. 5, 2003, pp. 1148-1149.

Krishnan, K.S., et al., "Perturbation of lipid structures by fluorescent probes: FEBES Letters," vol. 60, No. 2, Dec. 1975, pp. 419-422.

Krstic V., "Magneto-dynamics of chiral carbon nanotubes," Chemical Physics Letter, vol. 390, 2004, pp. 25-28.

Lakowicz, J.R., "Principles of Fluorescence Spectroscopy," Third Edition, Springer, 2006, ISBN 0387312781, pp. 353-382 (and figure 1).

Lim, S., "Ethambutol-associated Optic Neuropathy," Ann Aced Med Singapore, vol. 35, 2006. pp. 274-278.

Lin, J., et al., 01CA Practical Enantioselective Fluorescent Sensor for Mandelic Acid,01D J. Am. Chem. Soc., vol. 124, Issue 10, American Chemical Society (2002).

Manhas, S., et al., "Mueller matrix approach for determination of optical rotation in chiral turbid media in backscattering geometry", Jan. 9, 2006, vol. 14, No. 1, Optics Express, pp. 190-202.

McCarroll, M.E., et al., "Fluorescence Anisotropy as a Measure of Chiral Recognition," Journal of the American Chemical Society, 2001, vol. 123, pp. 3173-3174.

Moreira, A.B., "Direct determination of paracetamol in powdered pharmaceutical samples by fluorescence spectroscopy," Analytica Chimica Acta, vol. 539, 2005, pp. 257-261.

Narayanswamy, P.K., "The Raman spectra of water, heavy water and ice," Proceedings Mathematical Science, vol. 27, No. 4, 1948, pp. 311-315.

Nilsson, C., et al., "Nanoparticle-based pseudostationary phases in capillary electrochromatography," Electrophoresis., vol. 27, No. 1, 2006, pp. 76-83.

O'Connell, M.J., et al., "Chiral selectivity in the charge-transfer bleaching of single-walled carbon-nanotube spectra," Nature Materials, vol. 4, 2005, pp. 412-418.

Pike, J.P., "Fluorescence of mixed powder samples: a six-flux theory," Appl. Opt, vol. 20, 1981, pp. 1167-1173.

Roy, S., et al., "Nanoparticle induced conformational change in DNA and chirality of Silver Nanoclusters," Journal of Nanoscience and Nanotechnology, vol. 10, No. 2, 2010, pp. 819-825.

Spivey, A., 01CChemistry I (Organic): Stereochemistry Hybridisation and Molecular Shape: Enantiomers,01D pp. 5, http://www.ch.ic.ac.uk/local/organic/tutorial/ACS2.pdf.

US Notice of Allowance on U.S. Appl. No. 13/513,068 DTD Jun. 6, 2013.

US Notice of Allowance on U.S. Appl. No. 13/513,068 DTD Sep. 20, 2013.

US Office Action (Restriction Requirement) on U.S. Appl. No. 13/513,068 DTD Dec. 14, 2012.

US Office Action on U.S. Appl. No. 13/513,068 DTD Feb. 28, 2013.

Viedma, C., "Chiral symmetry breaking during crystallization: complete chiral purity induced by nonlinear autocatalysis and recycling." Physical review letters 94.6 (2005): 065504.

Wang, J.T., et al., Accurate Formulation of Faraday, Magnetic Circular Dichroism (MCD) and Kerr Effect of Light in Ferroelectromagnet, Journal of Superconductivity and Novel Magnetism, vol. 23, Issue 6, pp. 115-1160, Springer, (2010).

Wei, A., "Calixarene-encapsiluted nanoparticles: self assembly into functional nanomaterials," Chem Commun (Camb)., vol. 15, 2006, pp. 1581-1591.

Williams, A. A., "Determination of Enantiomeric Compositions of Analytes Using Novel Fluorescent Chiral Molecular Micelles and Steady State Fluorescence Measurements", J. Fluoresc. Mar. 2008; 18(2): pp. 285-296.

Sekhon, B.S., "Enantioseparation of Chiral Drugs—An Overview," International Journal of ParmTech Research, Apr.-Jun. 2010, vol. 2, No. 2, pp. 1584-1594.

Shemer, G., et al., "Chirality of Silver Nanoparticles Synthesized on DNA", J. Am. Chem. Soc. 2006, 128, pp. 11006-11007.

Spivey, A., 01CChemistry I (Organic): Stereochemistry Hybridisation and Molecular Shape: Enantiomers,01D pp. 5, http://www.ch.ic.ac.uk/local/organic/tutorial/ACS2.pdf, Jun. 17, 2004.

Stine, K.J., et al., "Comparison of Enantiomeric and Racemic Monolayers of N-Stearoylserine Methyl Ester by Fluorescence Microscopy," Langmuir, May 1993, vol. 9, pp. 2112-2118.

Sui, J., et al., Expanding proteomics into the analysis of chiral drugs Molecular BioSystems 5, Apr. 2009,: pp. 603-608.

Szollosi, G., "Preparation of Pt. Nanoparticle in the presence of a chiral modifier and catalytic applications in chemoselective and asymmetric hydrogenation," J Mater Chem., vol. 15, No. 25, 2005, pp. 2464-2469.

Torsi, L., et. al., "A sensitivity-enhanced field-effect chiral sensor," Nat Mater. vol. 7, No. 5, 2008, pp. 412-417.

Toukoniity, E., et al., "Catalyst selection and solvent effects in the enantioselective hydrogenation of 1-phenyl-1,2-propanedione," Studies in Surface Science and Catalysis, vol. 130, 2000, pp. 3363-3368.

Tran, C.D., et al., "Fluorescence determination of enantiomeric composition of pharmaceuticals via use of ionic liquid that serves as both solvent and chiral selector," Analytical Biochemistry, vol. 356, 2006, pp. 51-58.

(56) References Cited

OTHER PUBLICATIONS

Tsumator, H., et. Al., 01CObservation of Chiral Aggregate Growth of Perylene Derivative in Opaque Solution by Circularly Polarized Luminescence,01D Organic Letters, vol. 12, No. 10, pp. 2362-2365, American Chemical Society (2010).

US Notice of Allowance on U.S. Appl. No. 13/513,068 Dated Jun. 6, 2013.
US Notice of Allowance on U.S. Appl. No. 13/513,068 Dated Sep. 20, 2013.
US Office Action (Restriction Requirement) on U.S. Appl. No. 13/513,068 Dated Dec. 14, 2012.

* cited by examiner

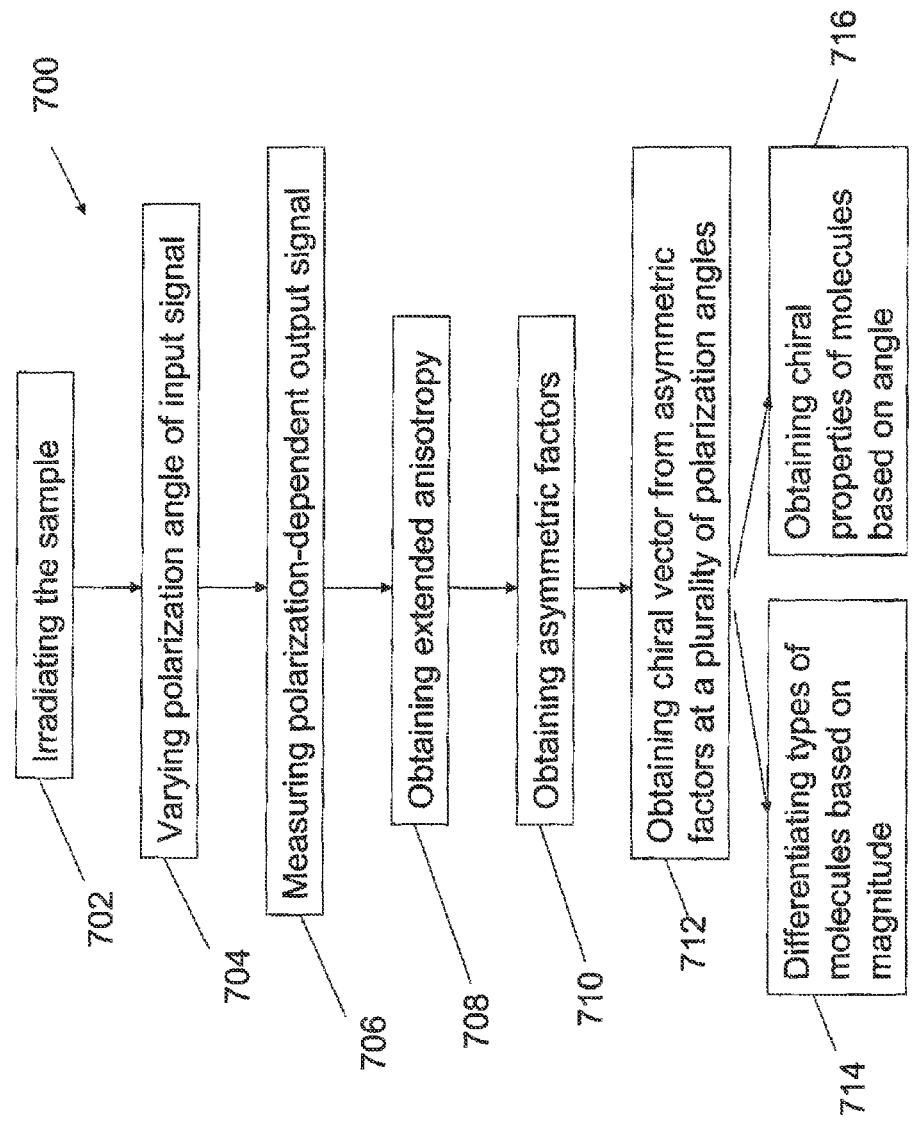

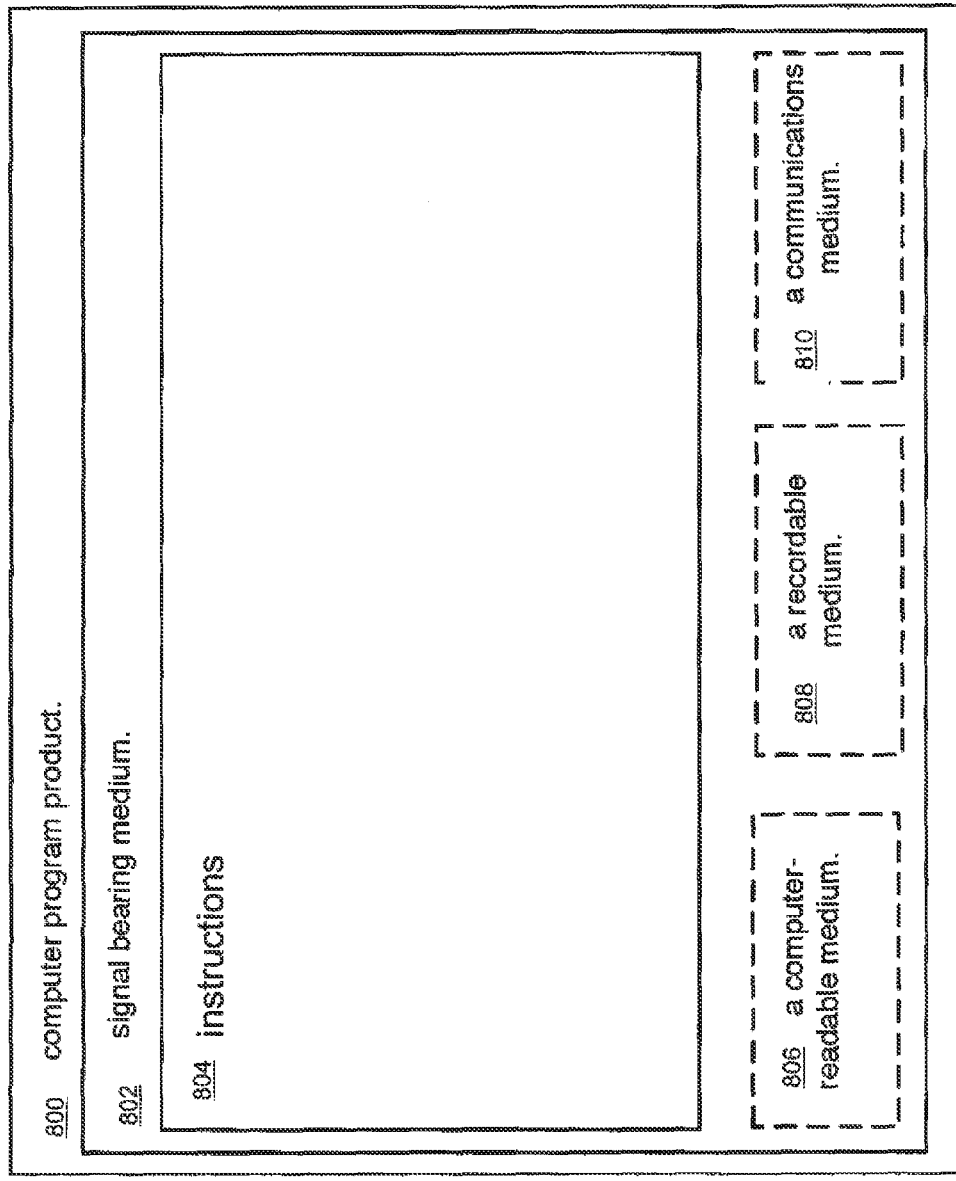

APPARATUS AND METHODS FOR CHIRALITY DETECTION

CROSS-REFERENCE TO RELATED APPLICATION

This present application is a divisional of U.S. patent application Ser. No. 13/513,068, filed May 31, 2012, now allowed, which is a U.S. National Stage of PCT International Application Number PCT/IB2011/001409, filed Jun. 21, 2011, which claims priority to a corresponding patent application filed in India and having application number 376/KOL/2011, filed on Mar. 21, 2011. The entire contents of the foregoing applications are herein incorporated by reference.

TECHNICAL FIELD

The present disclosure is directed to the detection of a chiral property of a material and separation of molecules based on their chiral properties.

BACKGROUND

Unless otherwise indicated herein, the materials described in this section are not prior art to the claims in this application and are not admitted to be prior art by inclusion in this section.

Technologies related to the chirality of materials started from the days of Pasteur's separation of single enantiomers using tweezers. Since then, automated systems and chiral catalysts have been developed to detect chiral properties of materials, separate enantiomers, and obtain end product with single handedness. Many modern drugs are synthesized from single isomers. Detrimental or inactive mirror images of certain molecules can be identified at an early stage in the development process.

The U.S. market for chiral compounds has an annual growth rate of 8.8%, and is expected to exceed $1.8 billion in the next few years. Due to their importance in pharmaceutical industries, methods of chiral detection and chiral detectors have received significant attention.

Much success has resulted from improvements in chiral analysis techniques using existing polarimetric principles. More specifically, efforts have been made in the area of reducing noise associated with the measurements of the additional optical rotation induced by a chiral sample. Electronic or optical filters are often used to reduce the noise. Dual-beam methods have been developed, for example through comparison with a reference cell, mixing out-of-phase sinusoidal signals, switching between a signal and a reference beam, or using a two-frequency laser source with two orthogonal linearly-polarized waves. These methods may be used to determine the displacement from the null point of optical transmission.

Pockets cell modulation is also used for differential chiral analysis in flow cells. Alternating irradiation of linearly-polarized and circularly-polarized lights is carried out. The method is capable of handling systems in which there is a kinetic development of an enantiomeric component. There also have been some improvements in chiral detectors related to an improved sample-cell-based system for non-contact, rapid, low-noise, and accurate screening of chiral samples.

One alternative solution is using chiral columns in which the stationary phase is maintained chiral. Another approach uses proteomic basis of chiral drug action. Alternatively, two-photon polarization second-harmonic generation (SHG) spectroscopy can be employed. The SHG method provides a label-free platform to study bio-molecular interactions, such as the interaction between melletin and bio-membranes.

The chirality and molecular recognition of biological molecules are thus becoming prerequisites for many types of assemblies. For these assemblies the receptors are playing a key role in molecular recognition. Thus, chirality is emerging as an essential criterion for life, as many macromolecules including protein, DNA, and various metabolites etc., are chiral in nature.

The chirality in nanotechnologics is also important in practical applications such as functional self assembly, enantioselective catalysis, separation, biosensing, and optical devices. Given the predominant molecular nature of chirality, its implementation at the nanoscale relies upon successful transfer of chirality of template materials into nano-building blocks, e.g., ligand chirality in the case of nanoparticles (NPs). There are many biological systems at microscopic and macroscopic levels which are enriched by chiral objects such as proteins, nucleic acids, carbohydrates, amino acids, and nucleotides.

SUMMARY

The inventors of the present application have recognized that existing methods do not provide solution for determining handedness of opaque and/or powdered substances, such as an insoluble rock material. For example, it would be difficult to determine enantiomeric properties of a chiral but opaque crystal. Conventional techniques such as circular dichroism or classical polarimetry cannot be used for opaque materials.

Technologies are generally described for systems and methods for detecting chiral properties of materials and separating materials based on their chiral properties. A chiral vector is constructed from anisotropic properties of a polarization-dependent output signal from a sample. Different types of molecules from the sample can be differentiated based on a magnitude of the chiral vector. Chiral properties of the sample can be detected based on an angle of the chiral vector. The output signal can be a fluorescent emission from the sample and can be used to detect chiral properties of a substantially opaque sample.

Devices and techniques described herein can be employed to determine the chirality of solid samples which are intrinsically fluorescent or which are tagged with achiral fluorescent molecules. A thin layer of the sample (e.g., immobilized on glass) can be mounted for measurement (e.g., inserted in a cuvette holder).

The making of novel chiral column materials, including for example synthetic materials with minimal opacity, would require a chirality monitoring of a different class. Embodiments disclosed herein, though based on an optical principle, can handle opaque and non-opaque samples, and can be scalable to various extents. A chirality vector is provided, of which both the magnitude and the direction are employed to derive properties of the sample. Embodiments disclosed herein may be of particular interest in exobiological searches, in novel nanomaterials, e.g., enantiomeric separation or identification of chiral carbon nanotubes.

In one aspect, a method is disclosed including detecting a chiral property of a sample from a fluorescent emission of the sample. In some embodiments the method may include irradiating the sample with an excitation beam, varying a polarization angle of the excitation beam, and measuring an intensity of the fluorescent emission as a function of a polarization angle.

Some embodiments include obtaining an extended anisotropic expression $A(\theta)$ defined as $$A(\theta) = \frac{I_{\theta,\theta} - I_{\theta,\theta+90°}}{I_{\theta,\theta} + 2I_{\theta,\theta+90°}}$$

where I is the intensity of the fluorescent emission measured at an excitation polarization angle θ (first subscript of I) and an emission polarization angle θ or θ+90° (second subscript of I). Some embodiments include obtaining a chirality vector from the fluorescent emission based on the extended anisotropic expression. In some embodiments, the obtaining a chirality vector includes obtaining asymmetric factors at a plurality of different fluorescent emission polarization angles.

In some embodiments, the plurality of different fluorescent emission polarization angles includes three or more angles. In some embodiments, the angles include 0°, 45°, and 90°. In some embodiments, the three angles include at least three different angles selected from 0°, 45°, 90°, 135°, 180°, 225°, 270°, and 315°.

In some embodiments, obtaining the asymmetric factors includes, for chiral fluorescent molecules, obtaining an extended anisotropy (X) at different excitation and fluorescent emission polarization angles; and obtaining a reciprocal of the extended anisotropy (X') at different excitation and fluorescent emission polarization angles. The obtaining the asymmetric factors further includes, for achiral fluorescent molecules, obtaining an extended anisotropy (Y) at different excitation and fluorescent emission polarization angles; and obtaining a reciprocal of the extended anisotropy (Y') at different excitation and fluorescent emission polarization angles. The obtaining the asymmetric factors further includes calculating the asymmetric factor (X−X')/(Y−Y').

Some embodiments include differentiating different types of molecules from the sample based on a magnitude of the chirality vector. In some embodiments, the chiral property is detected based on an angle of the chiral vector.

In some embodiments, the sample includes a substantially opaque material. In some embodiments, the substantially opaque material is in at least one of a solid, a liquid suspension, a semisolid, a powder, a crystalline, or a film form. In some embodiments, the substantially opaque material includes an opaque colloidal solution of a perylene derivative or derivatives.

In some embodiments, the sample includes a powdered material. In some embodiments, the powdered material includes one of glucose or fructose.

Some embodiments include attaching an achiral fluorescent tag to the sample. In some embodiments, the achiral fluorescent tag includes at least one of pyrene or biphenyl-4-carboxylic acid.

Some embodiments include controlling a process to obtain a product with a desired chirality state. In some embodiments, at least 100%, 99%, 90%, or 80% of the product is in the desired chirality state.

Some embodiments include irradiating the sample with an excitation beam. In some embodiments, the excitation beam is in the infrared, visible, ultraviolet or X-ray portion spectrum. In some embodiments, detecting a chiral property of a sample from a fluorescent emission of the sample includes measuring a polarization angular distribution of a Stokes line of the fluorescent emission.

Some embodiments include controlling an angular distribution of polarization of the excitation beam. Some embodiments include varying the polarization angle of the excitation beam. Some embodiments include separating molecules with predetermined handedness from the sample based on the detecting. Some embodiments include, producing a drug including the molecules with the predetermined handedness. Some embodiments include selecting a catalytic material including the molecules with the predetermined handedness. Some embodiments include selecting a chiral nanomaterial including the molecules with the predetermined handedness.

Some embodiments include irradiating the sample with an excitation radiation; and obtaining an angular polarization distribution of a Stokes line and an angular distribution of polarization of the excitation radiation. Some embodiments including measuring a polarization angle dependent intensity profile of the fluorescent emission.

In another aspect, an apparatus including: a sample holder configured to hold a sample; a radiation source configured to emit an excitation beam for causing a fluorescence emission of the sample; a first polarizer disposed between the radiation source and the sample holder and configured to control a polarization angle of the excitation beam; and a detector configured to detect the fluorescence emission indicative of a chiral property of the sample. Some embodiments include a second polarizer disposed between the sample holder and the detector and configured to determine a polarization dependence of the fluorescent emission.

In some embodiments, the sample includes a substantially opaque material. In some embodiments, the substantially opaque material is in at least one of a solid, a liquid suspension, a semisolid, a powder, a crystalline, or a film form.

Some embodiments include a device configured to control a process to obtain a product including a compound in desired chirality state. In some embodiments, at least 100%, 99%, 90%, or 80% of the compound in the product is in the desired chirality state.

In some embodiments, the radiation source is configured to emit the excitation beam in the infrared, visible, ultraviolet or X-ray portion of the spectrum.

In some embodiments, the detector is configured to measure an angular polarization distribution of a Stokes line of the fluorescent emission.

Some embodiments include a first actuator configured to actuate the first polarizer to vary an angular distribution of polarization of the excitation beam. Some embodiments include a second actuator configured to actuate the second polarizer.

Some embodiments include device configured to separate molecules having predetermined handedness from the sample based on the detection of the fluorescence emission indicative of a chiral property of the sample. In some embodiments, the device is further configured to produce a drug including the molecules having the predetermined handedness. In some embodiments, the device is further configured to select a compound including the molecules having the predetermined handedness. In some embodiments, the device is further configured to select a chiral nonmaterial including the molecules having the predetermined handedness.

In another aspect, a system is disclosed including: a sample holder configured to hold a sample; a radiation source configured to emit an excitation beam for causing a fluorescent emission of the sample; a first polarizer disposed between the radiation source and the sample holder and configured to control a polarization angle of the excitation beam; a detector configured to measure an intensity of the fluorescent emission; a second polarizer disposed between the sample holder and the detector and configured to control a polarization angle of the fluorescent emission; and a computer configured to derive a chiral property the sample based on the measured intensity.

The system of claim 54, where the computer is further configured to calculate an extended anisotropic expression A(θ) defined as:

$$A(\theta) = \frac{I_{\theta,\theta} - I_{\theta,\theta+90°}}{I_{\theta,\theta} + 2I_{\theta,\theta+90°}}$$

where I is the intensity of the fluorescent emission measured at an excitation polarization angle θ (first subscript of I) and an emission polarization angle θ or θ+90° (second subscript of I).

In some embodiments, the computer is further configured to calculate a chirality vector from the fluorescent emission based on the extended anisotropic expression. In some embodiments, the computer is further configured to: obtain the chirality vector by obtaining asymmetric factors at a plurality of different fluorescent emission polarization angles. In some embodiments, the plurality of different fluorescent emission polarization angles includes three angles. In some embodiments, the three angles include 0°, 45°, and 90°.

The computer is further configured to obtain the asymmetric factors by, for chiral fluorescent molecules, obtaining an extended anisotropy (X) at different excitation and emission polarizer angles; and obtaining a reciprocal of the extended anisotropy (X') at different excitation and emission polarizer angles. Further, the asymmetric factors are obtained by, for achiral fluorescent molecules, obtaining an extended anisotropy (Y) at different excitation and emission polarizer angles; and obtaining a reciprocal of the extended anisotropy (Y') at different excitation and emission polarizer angles. Further, the asymmetric factors are obtained by, calculating the asymmetric factor (X−X')/(Y−Y').

In some embodiments, the computer is further configured to distinguish different types of molecules from the sample based on a magnitude of the chirality vector. In some embodiments, the computer is further configured to derive the chiral property based on an angle of the chiral vector.

Some embodiments include a device configured to separate molecules having predetermined handedness from the sample based on the derived chiral property. In some embodiments, the device is further configured to produce a drug including the molecules having the predetermined handedness. In some embodiments, the device is further configured to select a catalytic material including the molecules having the predetermined handedness. In some embodiments, the device is further configured to select a chiral nanomaterial including the molecules having the predetermined handedness.

In another aspect, a non-transitory computer readable medium having instructions stored thereon is disclosed, where the instructions include: deriving a chiral property of a sample from a fluorescent emission of the sample.

In some embodiments, the deriving is based on calculation of an extended anisotropic expression A(θ) expression defined as:

$$A(\theta) = \frac{I_{\theta,\theta} - I_{\theta,\theta+90°}}{I_{\theta,\theta} + 2I_{\theta,\theta+90°}}$$

where I is the intensity of the fluorescent emission measured at an excitation polarization angle θ (first subscript of I) and an emission polarization angle θ or θ+90° (second subscript of I).

In some embodiments, the instructions further include calculating (or evaluation of) a chirality vector from the fluorescent emission based on the extended anisotropic expression. In some embodiments, the calculating a chirality vector includes obtaining asymmetric factors at a plurality of different fluorescent emission polarization angles. In some embodiments, the plurality of different fluorescent emission polarization angles includes three (or more) angles. In some embodiments, the three angles include 0°, 45°, and 90°.

In some embodiments, the instructions further include for chiral fluorescent molecules: obtaining an extended anisotropy (X) at different excitation and emission polarizer angles; and obtaining a reciprocal of the extended anisotropy (X') at different excitation and emission polarizer angles. In some embodiments, the instructions further include for a chiral fluorescent molecules: obtaining an extended anisotropy (Y) at different excitation and emission polarizer angles; and obtaining a reciprocal of the extended anisotropy (Y') at different excitation and emission polarizer angles. In some embodiments, the instructions further include calculating the asymmetric factor (X−X')/(Y−Y').

In some embodiments, the instructions further include distinguishing different types of molecules from the sample based on a magnitude of the chirality vector. In some embodiments, the deriving a chiral property is based on an angle of the chiral vector.

In another aspect, a method is disclosed including: measuring a polarization-dependent output signal from a sample; obtaining a plurality of asymmetric factors based on anisotropy properties of the output signal at a plurality of polarization angles; and constructing a chiral vector using the asymmetric factors as components corresponding to the plurality of polarization angles. Some embodiments include differentiating types of molecules from the sample based on a magnitude of the chiral vector. Some embodiments include obtaining chiral properties of the sample based on an angle of the chiral vector. In some embodiments, the anisotropy properties are obtained from the output signal at various polarization angles. In some embodiments, the plurality of asymmetric factors is obtained from the anisotropy properties and reciprocals of the anisotropy properties for chiral molecules and comparison achiral molecules.

In some embodiments, the output signal includes one of chemiluminescence, phosphorescence, radioisotope emission, particle bombardment caused emission, scattering, transmission, absorption, or reflection signals.

In some embodiments, the output signal includes one of a fluorescent emission, and where the method further includes irradiating the sample with an excitation radiation.

In some embodiments the sample is a partially or substantially opaque sample.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIG. 2A and FIG. 213 are plots showing the intensity profile of the chiral molecule tyrosine as a function of polarization angle, for different excitation polarization angles;

FIG. 7 is a flowchart illustrating a method for constructing the chiral vector and for detecting chiral properties of the sample; and FIG. 8 is a block diagram illustrating a computer program product for analyzing the output signal from the sample to obtain the chiral properties.

DETAILED DESCRIPTION

Figure 1:
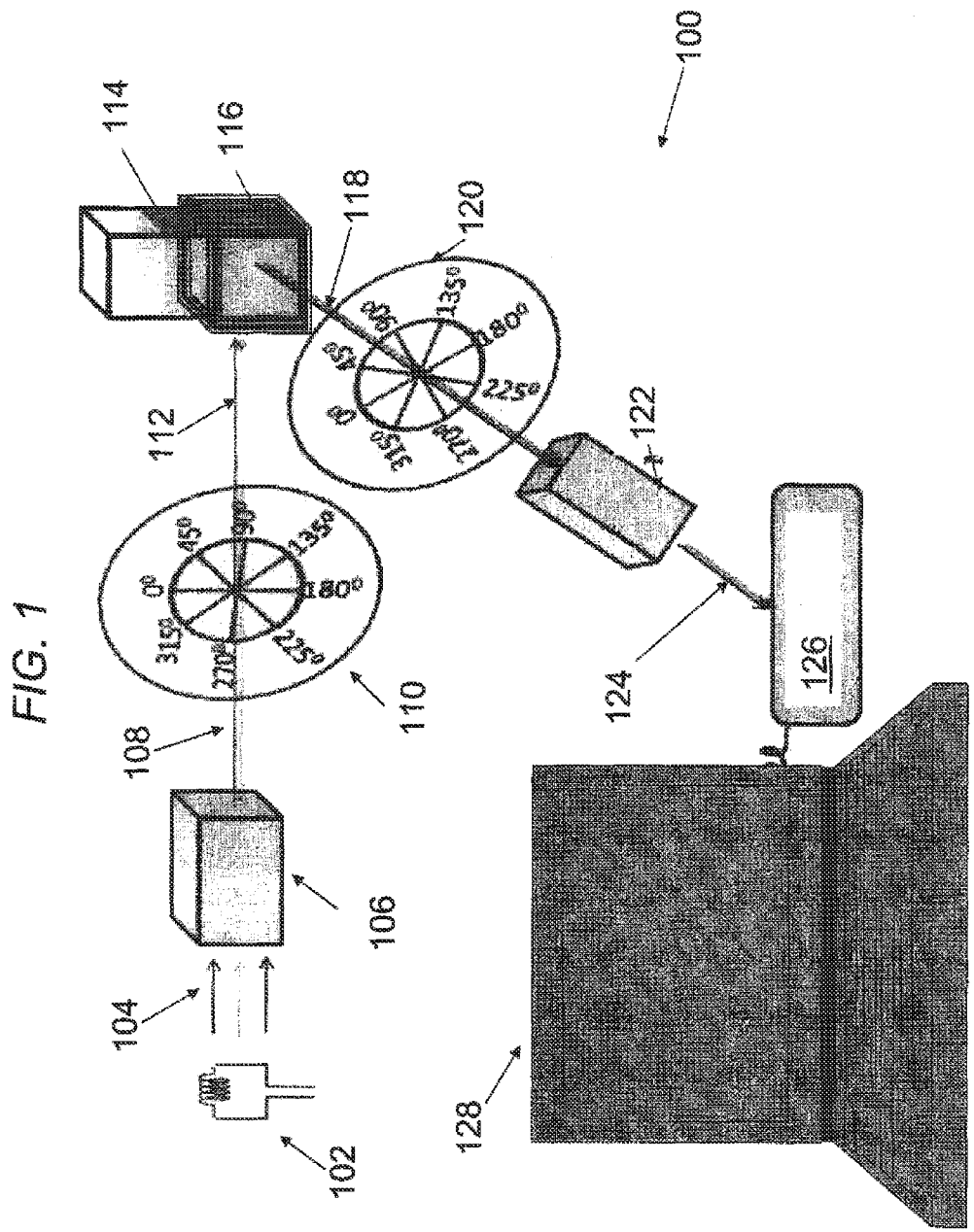
FIG. 1 is a schematic diagram illustrating a system for detecting chiral properties of a sample.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Methods, apparatus, systems, devices, and computer program products related to detection and measurements of chirality of substances, such as opaque materials are disclosed.

It is noted that under normal circumstances the probabilities of emergence of the two enantiomers are identical. Thus, selection mechanisms are needed to select one from the other. Enantiomeric selection (selection of a given handed molecule out of its two non-superimposable mirror images) has been a challenging problem in stereochemistry. There are few techniques to quantify and segment chiral molecules from their mirror images. The ubiquitous presence of chirality in biology remains unexplained. Chirality is also experimentally difficult to measure, and only a few techniques limited to measurement of chirality of transparent samples.

Despite the challenges, chirality has very useful applications in pharmaceutical industries and drug research. A given enantiomer (molecule with handedness) may have more biological activities as a drug, as compared to its mirror image. The mirror image molecule may even have adverse effects. A classical example of an enantiomeric drug molecule is thalidomide, of which one enantiomer is useful in treating morning sickness during pregnancy, while the other enantiomer can cause birth defects (a fact that was known for a long time). Other enantiomeric drugs include ethambutol, naproxen, etc. Each of these molecules has only one mirror image form that is active as a drug.

With the advent of nanomedicine, chirality nanostructures is also under extensive oldies.

In addition to drug discovery, enantiomeric selection may be important in the discovery of novel catalytic materials. Loading of platinum (Pt), for example, is known to enhance enantio-differentiation in a size-dependent fashion. Chirality of opaque, rock-Re materials can be useful in the study of many geo-biochemical and exo-biological subjects.

Existing methods, e.g., polarimetry or circular dichroism (CD), may not be useful for measurements of chirality of opaque substances in solid or powder forms. It is also difficult to realize miniaturization of the equipment in these methods.

Briefly stated, technologies are generally described herein for systems and methods for detecting chiral properties of materials and separating materials based on their chiral properties. A chiral vector is constructed from anisotropy properties of a polarization-dependent output signal from a sample. Different types of molecules from the sample can be differentiated based on a magnitude of the chiral vector. Chiral properties of the sample can be detected based on an angle of the chiral vector. The output signal can be a fluorescent emission from the sample and can be used to detect chiral properties of a substantially opaque sample.

Embodiments disclosed herein provide apparatuses and methods for measuring chiral fingerprints, and for comparing the extent of symmetry breaking among different chiral molecules. Asymmetry indicates that a molecule has a mirror image that is not superimposable. The molecule can have a proper rotational axis ($C_n$, where n=1), and thus can be said to be chiral. An example of such a molecule can have the following form:

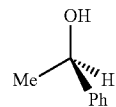

Dissymmetric molecules refer to those having a proper rotational axis ($C_n$, where n is an integer larger than 1). Such molecules are also known as chiral molecules. An example of such molecules can have the form:

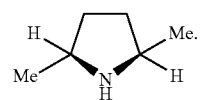

Some chiral molecules, such as spiranes, lack a traditional chiral center. Spiranes are a class of compounds having two rings with one carbon atom in common. This makes the rings perpendicular, and suitable substitution gives rise to chirality. So too can an exocyclic double bond. The compounds below display these features and are chiral.

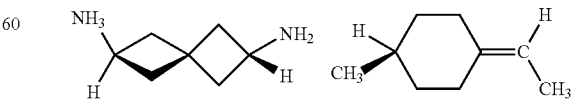

In the measurements described herein, the detected asymmetry does not depend on the amount of the sample or the emission intensity, so long as the intensity is above the detection sensitivity limit of the instruments. Thus, the asymmetry is a scale-free property of materials.

In various embodiments, apparatuses of the type described herein can be operable at an ultra-low scale if needed, and can be employed to detect chirality of semisolid, powdered, or opaque samples, in some embodiments, the apparatus can be miniaturized by scaling down the physical dimensions of the components. Bulky instruments typical in conventional CD methods are no longer needed.

Examples of opaque colloidal solution suitable for testing include, but are not limited to, perylene derivatives. Other examples of powdered chiral molecules suitable for testing include, but are not limited to, carbohydrate molecules such as glucose, fructose, etc.

A number of methods have recently been proposed to address chirality or molecular dissymmetry. Single molecule spectroscopy, for example, probes the role of local molecular environments inducing chirooptical response in isolated molecular systems. Ionic liquids have been used for determining enantiomeric compositions of various drugs. The effectiveness of RTIL (chiral room temperature ionic liquid) in obtaining chiral pharmaceutical products has been shown.

Although fluorescence of powdered sample for excitation in UV and visible portion of the spectrum or X-Ray portion of the spectrum (e.g., for rocks and minerals) has been reported, no attempts have been made to analyze the enantiomeric distribution of such samples.

The relative variation of fluorescence including variation in excitation and emission polarizing angle has been studied for various materials, yet this property has not been used to probe into the chiral behavior of non-fluid samples.

In one embodiment, a scale-free description of the enantiomeric state or distribution is provided irrespective of the opacity of the samples. In some embodiments, a chiral vector concept is introduced, which can express and classify different chiral substances in terms of a metric.

A method according to one embodiment can fingerprint the chirality of test molecules, and provide an index vector revealing the degree of symmetry breaking between such molecules. In one example, the method is based on comparison of angular distribution of Stokes line. Angular distribution of polarization of an incident light beam and that of an emitted Stokes line can carry the chirality signature. The emission intensity, an implicit function of an angle, satisfies at least three mirror symmetry elements from 0-360° in the emission distribution plane. The broken symmetry of the angular distribution can then be fused into a vector whose magnitude reflects the cumulative extent of symmetry breaking. The direction of the vector reflects the polarization angle that contributes maximally to the broken symmetry of the molecules in question. For achiral molecule, this vector will be a null vector. The method can be applied to enantiomeric selection of test molecules in liquid suspension, in a powder form, as films, or in a crystalline form.

For opaque materials, one method disclosed herein uses polarized excitation with varying excitation angles to excite the sample to cause fluorescent emission. Similarly, polarized emission is obtained by varying the polarizer angles. Because fluorescence can be detected even for solid substances in the forms of powder or films, the validity of the method is not confined to only liquid states.

In a representative embodiment, fluorescence from a sample is examined at varying angles of excitations and emissions and used to detect a chiral property of a sample. In the case that the sample is not fluorescent, an achiral fluorescent tag, e.g., pyrene biphenyl-4-carboxylic acid can be attached. Symmetry of the angular profile of the emission intensity for a given couplet of excitation and emission polarizer angles provides information on the chiral nature of the sample under examination. Unlike conventional techniques, measurements based on fluorescence emission of samples do not require the samples to be in liquid or gaseous state. Thus, chiral properties of solid or powdery samples cm be measured based on polarized fluorescence emission. An integrating sphere as known to those of ordinary skill in the art (e.g., of the type available from Newport Corporation of 1791 Deere Avenue, Irvine Calif. 92606, USA) can be used to measure the fluorescence emissions from such samples.

An integrating sphere (also known as an Ulbricht sphere) is an optical component consisting of a hollow cavity with its interior coated for high diffuse reflectivity (i.e., white), having relatively small holes as needed for entrance and exit ports. The shape of the cavity is commonly spherical. The integrating sphere is characterized by a uniform scattering or diffusing effect. Light rays incident on any point on the inner surface are, by multiple scattering reflections, distributed equally to all other such points and effects of the original direction of such light are minimized. An integrating sphere may be thought of as a diffuser which preserves power but destroys spatial information. Accordingly, when measuring fluorescence of a solid sample (e.g., a thin film), an integrating sphere may be used to compensate for spatially inhomogeneous fluorescence emissions (e.g., caused by waveguiding effects in the sample).

General Procedures for Measuring Chirality

FIG. 1 is a schematic diagram illustrating a system 100 for measuring chiral properties of a sample. The system 100 includes a radiation source 102, such as a Xenon lamp, to generate an excitation radiation 104, such as light in the UV range. In some other embodiments, an X-ray source, a source of particle (e.g., electron) beam, or other types of radiation sources can be used.

The excitation radiation 104 goes through a first, excitation-side, monochromator 106 and becomes a radiation beam 108 having a narrow spectral range. The radiation beam 108 goes through a first, excitation-side, polarizer 110, and becomes a polarized excitation beam 112. The excitation-side polarizer 110 can be actuated by a first actuator (not shown), and used to control a polarization angle of the excitation beam 112. The polarized excitation beam 112, of which an angular distribution of polarization can be varied, excites a sample 114 disposed in a sample holder 116, and causes a fluorescence emission 118 from the sample 114. The sample 114 can be, for example, a substantially opaque material. The sample can be, for example, in a solid, a liquid suspension, a semi-solid, a powder, a crystalline, or a film form. The sample holder 116 can be, for example, a cuvette holding the sample. In some embodiments, the sample may be disposed as a thin film on a substrate, e.g. a microscope slide. For example, in the case of a solid sample, a thin layer of the sample (e.g., immobilized on glass) can be mounted for measurement (e.g., inserted in a cuvette holder). In one example, the fluorescence emission 118 includes a Stokes line from the sample 114.

The fluorescence emission 118 goes through a second, emission-side, polarizer 120, and a second, emission-side monochromator 122. The emission-side polarizer 120 can be actuated by a second actuator (not shown). By varying a polarization angle to thereby pass through the emission component with the specified polarization angle, the emission-side polarizer 120 can be used to determine the polarization dependence, or angular distribution, of the fluorescence emission 118. The substantially monochromatic emission 124 carrying the polarization information is detected by a detector 126. The detected signal is analyzed by a computer 128.

In various embodiments, for a given angle for the excitation side polarizer 110, the emission side polarizer 120 may be controlled to obtain measurements at a set of desired angular configurations. For example, in some embodiments, measurements can be made with the emission side polarizer 120 at angles of 0°, 45°, and 90°. In other embodiments, any suitable choice of angles may be used. For example, any angles from 0° to 360° that are multiples of 0°, 45°, and 90° can be used. In various embodiments, angles other than multiples of 45° may be chosen, e.g., multiples of 30° (30°, 60°, 90°, 120°, ..., 360), multiples of 20 degrees (20°, 60°, 80°, 100°, 120°, ..., 360). In some embodiments, a 45° interval is used to minimize the time for data collection and to provide a simple basis for construction of the chirality vector, as described in detail below.

Because the detected anisotropy is a scale-independent quantity, small samples may be used. Further, some or all of the components of system 100 may be miniaturized and provided in a compact form factor. For example, in one embodiment, radiation source 102 may be a laser diode which produces monochromatic output, such that excitation-side, monochromator 106 may be omitted. The remaining elements including polarizers 110 and 120, monochromator 122, and detector 126 may be miniaturized optical elements. In some embodiments, a portion or all of the system is composed of an integrated optical device or photonic integrated circuit.

The apparatus can further include a device configured to control a process to obtain a product comprising molecules in desired chirality state. The product can be, for example, a compound, a drug, or a nanomaterial comprising the molecules having the predetermined handedness. Such a device is generally known to those of ordinary skill in the art to separate a compound in desired chirality state from the sample 114 based on the detected chirality properties of the sample 114. In one example, 100% of the compound in the product is in the desired chirality state. In another example, 99% of the compound in the product is in the desired chirality state. In another example, 90% of the compound in the product is in the desired chirality state. In another example, 80% of the compound in the product is in the desired chirality state.

In one experimental study, higher than 90% purity of enantiomeric forms of amino acids may be measured. Even if the chiral impurity, or extent of racemization is <=10%, the method can still be used. The ability to detect an enantiomeric compound is very high, as the technique is sufficiently sensitive to permit detection even in the presence of considerable extent of enantiomeric impurity.

The enantiomeric purity index can be derived from the locus of the chiral vectors (as described below) with different measured degree of enantiomeric purity. As a result, enantiomeric drugs of high purity can be produced and/or separated from the sample 114.

In some embodiments, the system 100 detects chiral properties of a sample and/or to separate molecules based on their enantiomeric configurations. The system 100 can include a computer 128 configured to derive a chiral property the sample based on the measured intensity of the fluorescence emission 118.

In accordance with some embodiments disclosed herein, the conventional anisotropy expression is extended to take into account the varying excitation angles. For example, with reference to FIG. 1, in an anisotropy measurement, the sample 104 can be excited with a vertically polarized light 112, and the intensity of the emission is measured parallel (∥) with respect to excitation polarizer 110 (termed as $I_\parallel$). Similarly, when the emission is measured perpendicular (⊥) with respect to the excitation emission, the intensity is termed as $I_\perp$. Hence mathematically the anisotropy A can be defined as: $A=(I_\parallel - I_\perp)/(I_\parallel + 2I_\perp)$.

Alternatively, anisotropy can be defined as the following to minimize the error occurred due to polarizer or instrument: $A=[I_{VV}-G^*I_{VH}]/[I_{VV}+2G^*I_{VH}]$, where G is a constant and is the ratio of the sensitivities of the detection system for vertically- and horizontally-polarized light. G can be represented by the following equation: $G=I_{HV}/I_{HH}$. Typically $G=1$.

To convert the above anisotropy equation into angles for measurements, denoting the vertical component V→0° and H→90° with respect to vertical excitation, $A=[I_{0ex0em}-G\ I_{0ex90em}]/[I_{0ex0em}+2G\ I_{0ex90em}]$ and $G=I_{90ex0em}/I_{90ex90em}$ where "ex" represents the excitation angle and "em" represents the emission angle.

The above mathematical expression of anisotropy involves only 0° and 90° polarizers for excitation and emission, but can be extended to an arbitrary angle θ for varying excitation and emission polarizers. Accordingly, an extended anisotropy for angle θ can be defined as a function of angles between 0° and θ+90°. That is, the conventional definition of anisotropy:

$$A = \left| \frac{I_{vv} - I_{vh}}{I_{vv} + 2I_{vh}} \right|$$

is extended to become the extended anisotropy to take into account the varying excitation angles:

$$A(\theta) = \left| \frac{I_{\theta\theta} - I_{\theta,\theta+90}}{I_{\theta\theta} + 2I_{\theta,\theta+90}} \right|.$$

In the extended anisotropy expression, wherein I is the intensity of the fluorescent emission, θ as the first subscript of I is a variable excitation polarization angle, and the second subscript of I is an emission polarization angle. For example, $I_{\theta\theta}$ refers to the fluorescent emission intensity measured when the emission polarizer is at a polarization angle θ, i.e., the same as the excitation polarization angle. $I_{\theta,\theta+90}$ refers to the fluorescent emission intensity measured when the emission polarizer is at a polarization angle θ+90, i.e., orthogonal to the excitation polarization angle.

The extended anisotropy of achiral molecules is used as a standard for comparison with chiral molecules. The ratio is plotted to reflect the asymmetry of arms of the M-like pattern. Comparison of FIG. 2A and FIG. 2B (showing intensity patterns for a chiral molecule), and FIG. 3 (showing intensity patterns for an achiral molecule), discussed in the detail in the Examples below, highlights the deviations in the arms of the "M." The transformations described in FIG. 4 leads to a clear distinction of the L-forms and D-forms.

Figure 4:
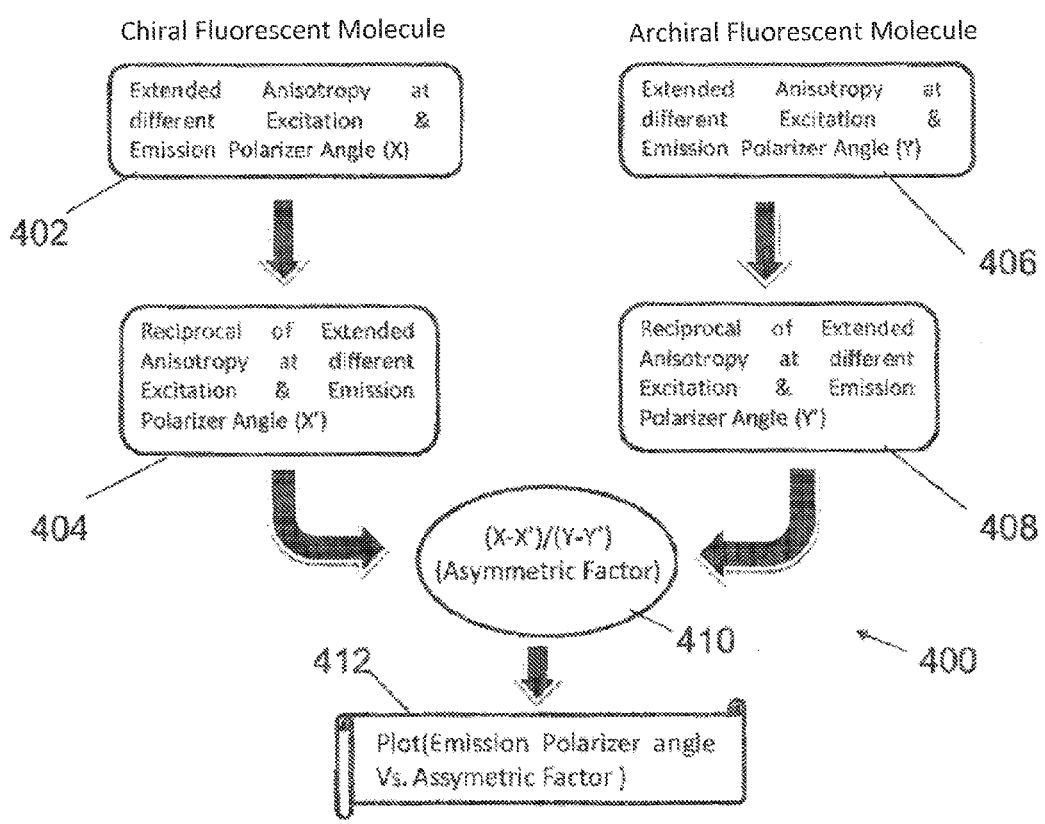
FIG. 4 is a flowchart illustrating a method for obtaining an asymmetric factor to analyze chirality.

FIG. 4 is a flowchart illustrating a method 400 of obtaining an asymmetric factor in accordance with one embodiment, using both chiral fluorescent molecules and achiral fluorescent molecules. Specifically, the method 400 includes, for chiral molecules, in operation 402, obtaining an extended anisotropy (X) at different excitation and fluorescence emission polarization angles; and in operation 404, obtaining a reciprocal of the extended anisotropy (X') at different excitation and fluorescent emission polarization angles.

The method 400 also includes, for achiral fluorescent molecules, in operation 406, obtaining an extended anisotropy (Y) at different excitation and fluorescent emission polarization angles, and in operation 408, obtaining a reciprocal of the extended anisotropy (Y') at different excitation and fluorescent emission polarization angles.

Figure 5A:
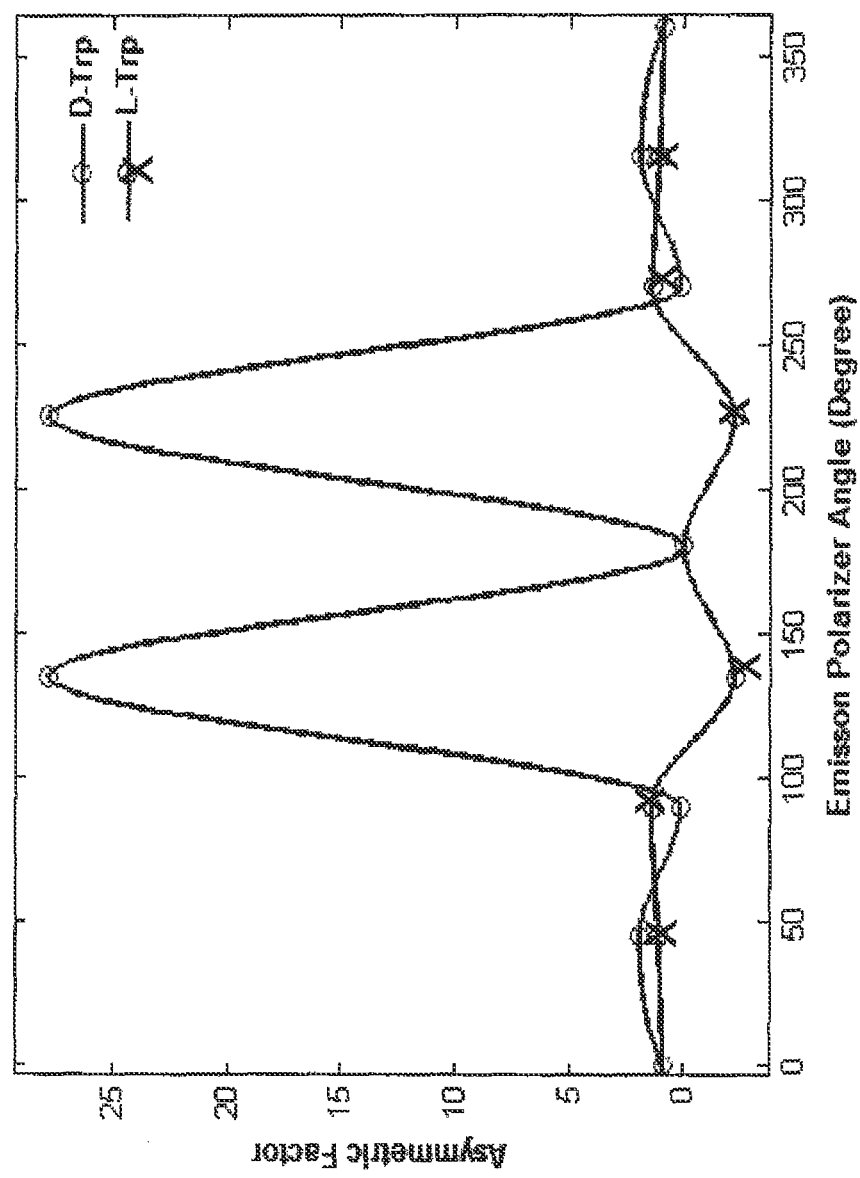
FIG. 5A, FIG. 5B, and FIG. 5C are plots showing chirality of tryptophan, phenylalanine, and tyrosine, respectively.
Figure 5B:
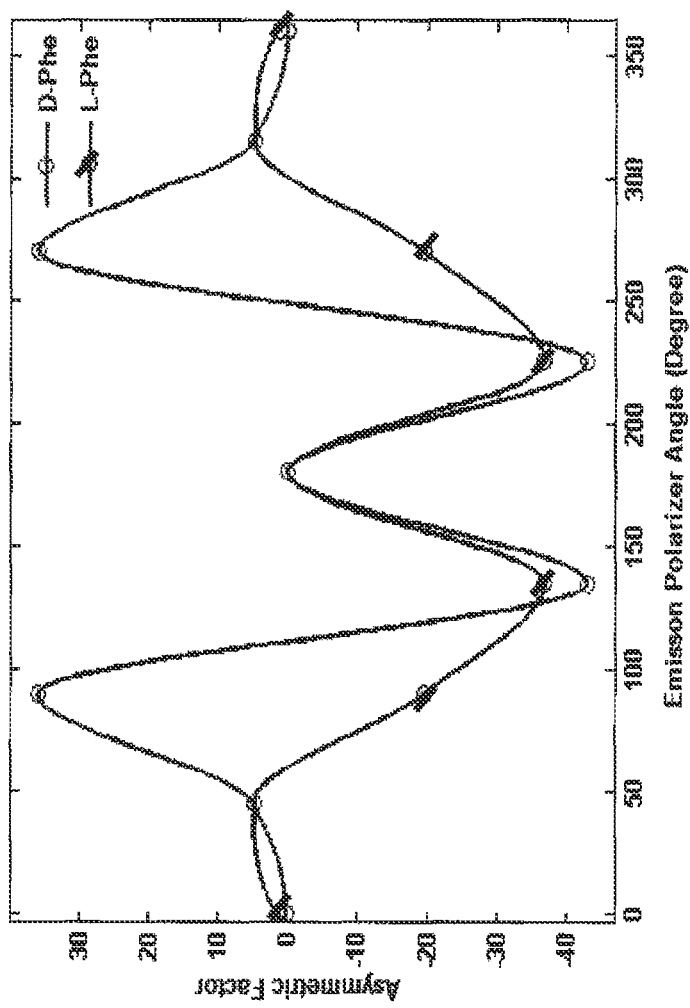
Figure 5C:
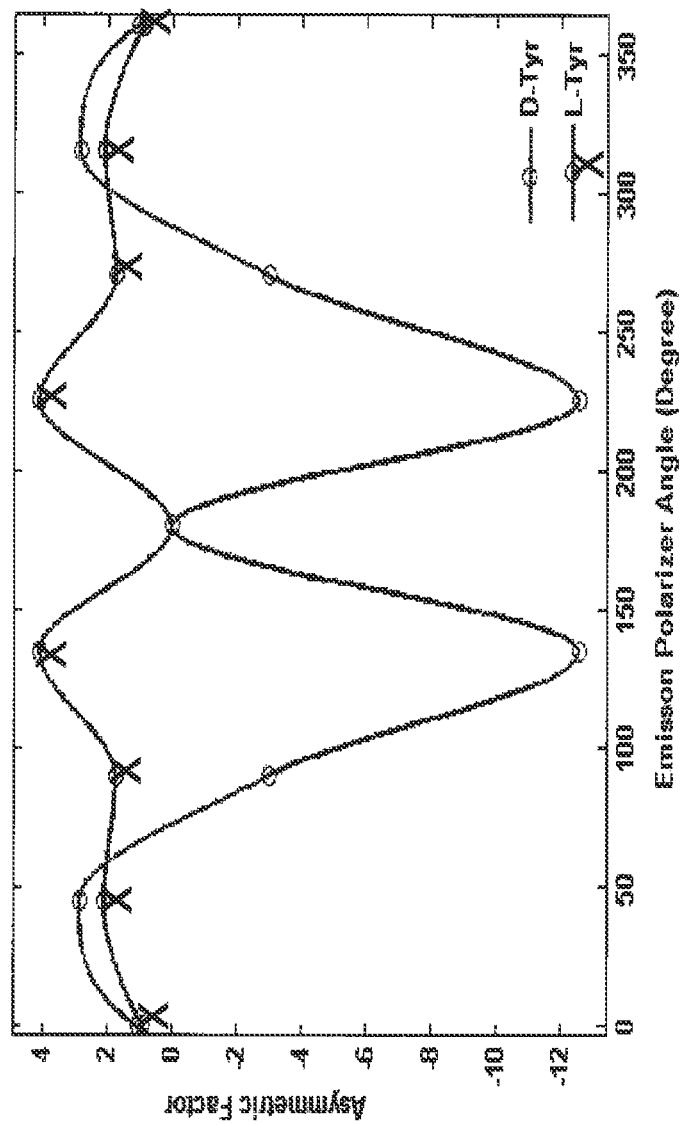
Figure 6:
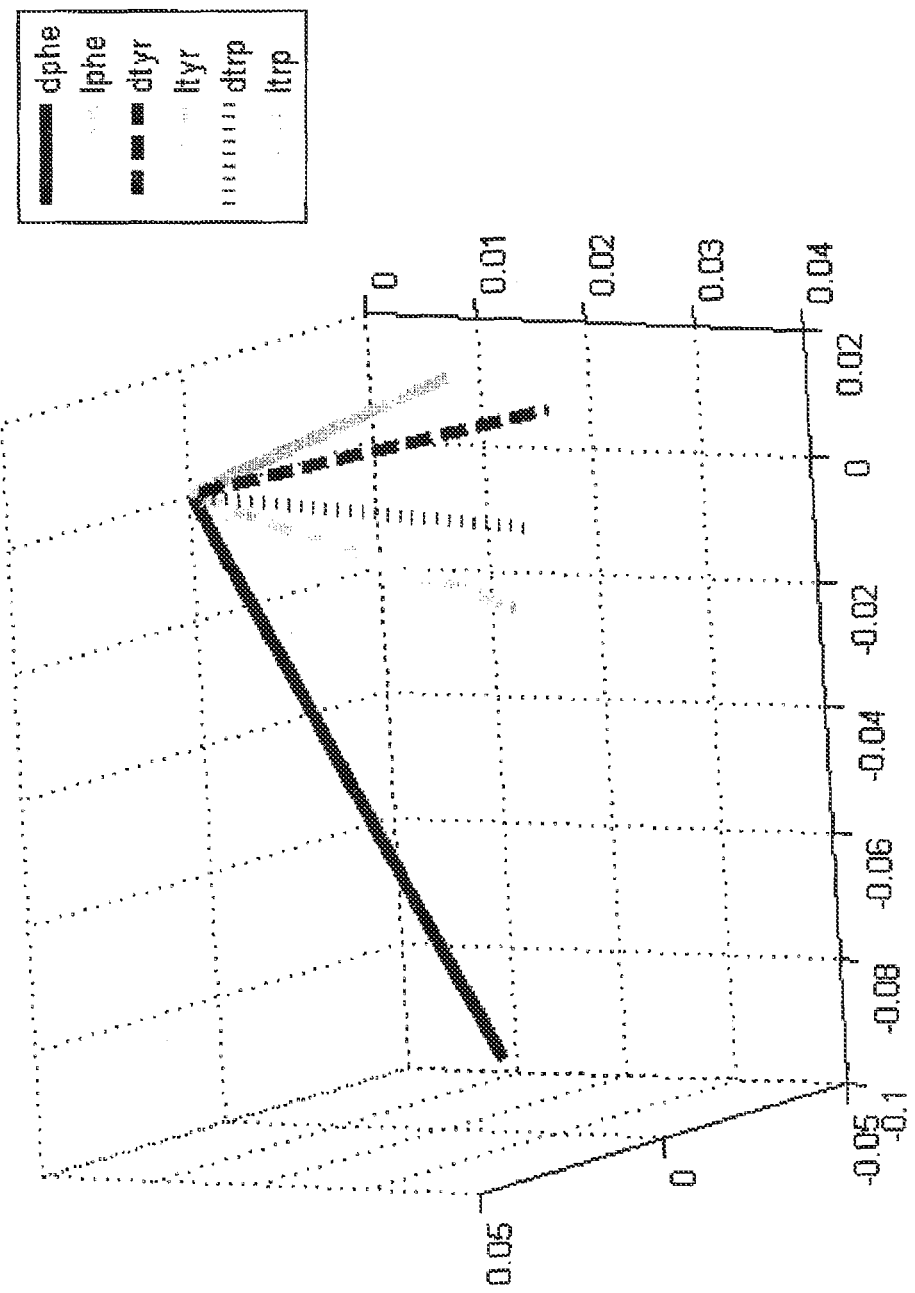
FIG. 6 is a plot illustrating the chiral vector of a sample, where the three components represent the asymmetries at three different emission polarization angles (0°, 45°, and 90° respectively)

The method 400 further includes, in operation 410, calculating the asymmetric factor (X-X')/(Y-Y'). In operation 412, the asymmetric factor can be plotted as a function of emission polarizer angle. Examples of such plots are shown in FIG. 5A, FIG. 5B and FIG. 5C, discussed in detail with reference to the Examples section provided below. The asymmetric factors may also be further processed, e.g., to provide a chiral vector (examples of which are shown in FIG. 6), as discussed in detail below.

Method to Measure and Analyze Chirality

A method 700 of detecting a chiral property of a sample and obtaining a product with a desired chirality state in accordance with one embodiment is summarized below with reference to the flowchart of FIG. 7.

In operation 702, the sample is irradiated. In the example described above with reference to FIG. 1, the sample is irradiated with an excitation radiation, and the chiral properties of the sample are detected based on fluorescent emission of the sample excited by the excitation radiation. However, it is noted that in some other embodiments, chemiluminescence, phosphorescence, radioisotopes, particle bombardment, scattering, transmission, absorption, or reflection be employed to measure the chiral properties and to obtain the chiral vector, so long as polarization information can be obtained from the sample.

In operation 704, a polarization angle of the input signal, such as the excitation beam, is varied. It is noted that in some embodiments, such as when chemiluminescence is employed, this operation is not needed, and the anisotropy is measured as a function of the emission polarization angle ($\theta_g$) instead of $\theta$ as described above, where $\theta$ involves both excitation and emission polarization angles.

In operation 706, the polarization-dependent output signal from the sample is measured using a detector. This involves, for example, measuring an intensity of the fluorescent emission as a function of a polarization angle. In operation 708, an extended anisotropy is obtained based on the output signal.

In operation 710, the asymmetric factors are obtained based on the extended anisotropy, as described earlier with reference to FIG. 4. In operation 712, a chiral vector is constructed from the asymmetric factors at a plurality of polarization angles. In operation 714, different types of molecules are differentiated based on the magnitude of the chiral vector, and in operation 716, chiral properties of the molecules are obtained based on the angle of the chiral vector.

Techniques for Measuring Samples with Mixed Chirality

In some embodiments, the techniques described herein may be used to determine the degree of chirality of a sample containing a potential mixture of molecules with opposite chirality types. Initially, the chirality vector of each of two references samples is measured. The chirality vector for the first and second reference samples will be referred to, respectively, as $V_1$ and $V_2$. The reference samples are each of the same substance of interest (e.g., tryptophan) but have substantially pure chirality (e.g., a sample of D-Trp and a sample of L-Trp).

The chirality vector $V_{exp}$ of the mixed sample (e.g., mixed D-Trp and L-Trp) is then measured using the techniques described herein. A unit vector $n_{exp}$ is constructed by normalizing $V_{exp}$. To determine the degree of chirality of the mixed sample, the normalized vector $n_{exp}$ is expressed in terms of the reference vectors $V_1$ and $V_2$ $$n_{exp} = \frac{aV_1 + (1-a)V_2}{|V_{exp}|}$$

where a is a constant value that may be solved for using the above equation and that indicates the degree of chiral purity of the mixture. That is, when a is equal to unity, the potentially mixed sample is composed substantially entirely of molecules have the same chirality as the first reference sample. When a is equal to zero, the potentially mixed sample is composed substantially entirely of molecules have the same chirality as the second reference. When a takes on a value between 0 and 1, the sample has mixed chirality.

In various embodiments, this measurement technique may be used to measure or monitor the chiral purity of a sample. This information may be used, e.g., to provide quality assurance for a material production process.

Kinetic Measurements

In some embodiments, the chirality vector of a sample may be measured repetitively (or even continuously) over time. This allows the monitoring of the kinetics of a chiral synthesis in a reaction. For example, if only one chiral substance is produced in a reaction, the measured chiral vector will have a constant direction, but charming magnitude. Similarly, the production of multiple chiral substances in a reaction may be identified as a change in the chiral vector of a sample over time.

In various embodiments, the chiral vector may be monitored and used to provide feedback to control the reaction under study. For example, a processor may monitor the measured chiral vector and control one or more heaters to vary the temperature of the reaction under study based on the magnitude and/or direction of the vector (or rates of change thereof, etc.). In various embodiments, any other suitable reaction parameters may be controlled.

In some embodiments, the chirality vector of a mixed sample may be measured over time and compared to reference vectors as described above to determine the degree of chirality of the mixed sample. Thus, in some embodiments, real time monitoring of the chiral purity of a sample undergoing a reaction may be provided. In some embodiments, this information may be used to control the reaction.

Computer Program Product for Analyzing Chirality

FIG. 8 is a block diagram illustrating an example computer program product 800 for use in the system particularly the computer 128 described above. The computer program product 800 can include a signal bearing medium 802, which can comprise a non-transitory computer readable medium 806, such as, but not limited to, a hard disk drive, a Compact Disc (CD), a Digital Video Disk (DVD), a digital tape, memory, etc. The computer program product 800 may also include a recordable medium 808, such as, but not limited to, memory, read/write (R/W) CDs, R/W DVDs, etc. In some implementations, the signal bearing medium 802 may encompass a communications medium 810, such as, but not limited to, a digital and/or an analog communication medium (e.g., a fiber optic cable, a waveguide, a wired communications link, a wireless communication link, etc.). Thus, for example, the computer program product 800 may be conveyed to one or more modules of the system by a radio frequency (RF) signal bearing medium 802, where the signal bearing medium 802 is conveyed by a wireless communications medium 810 (e.g., a wireless communications medium conforming with the IEEE 802.11 standard). Instructions 804 are stored in the signal bearing medium 802 to direct the system to perform the image processing, automated dose extraction, and reporting as described above. The computer storage media include, but are not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information.

The instructions stored in the non-transitory computer readable medium may include deriving a chiral property of a sample from a fluorescent emission of the sample. In one embodiment, the deriving is based on calculation of an extended anisotropic expression. The instructions can further include calculating a chirality vector from the fluorescent emission based on the extended anisotropic expression. The calculation of the chirality vector includes obtaining asymmetric factors at a plurality of different fluorescent emission polarization angles, in some embodiments, the plurality of different fluorescent emission polarization angles includes three angles, for example. The three different emission polarization angles can be 0°, 45°, and 90°, or any angles between 0° and 360° that are multiples of 0°, 45°, and 90°, i.e., 0°, 45°, 90°, 135°, 180°, 225°, 270°, and 315°. As described above, any other suitable choice of angles may be used.

The instructions can further include, for chiral fluorescent molecules: obtaining an extended anisotropy (X) at different excitation and emission polarizer angles, and obtaining a reciprocal of the extended anisotropy (X') at different excitation and emission polarizer angles; for achiral fluorescent molecules: obtaining an extended anisotropy (Y) at different excitation and emission polarizer angles; and obtaining a reciprocal of the extended anisotropy (Y') at different excitation and emission polarizer angles; and calculating the asymmetric factor (X−X')/(Y−Y').

The instructions can further include distinguishing different types of molecules from the sample based on a magnitude or direction of the chirality vector and deriving a chiral property is based on an angle of the chiral vector.

Advantages of some embodiments disclosed herein may include, for example, the apparatus and methods disclosed herein can be applied in various fields, such as analytical chemistry, and pharmaceutical industries. Miniaturized detection of chiral molecules or nanostructures can be realized using the methods and apparatus. The material under examination can be in liquid, solid, crystalline, powder, or thin film form. In various embodiments, any sample preparation techniques known in the art may be used, e.g., those described in Castiglioni et al., Chirality, Volume 12, pages 291-294 (2000) and Sparks, et al., Journal of Quantitative Spectroscopy& Radiative Transfer Volume 110, pages 1771-1779 (2009).

The method can quantify the degree of symmetry breaking using a simple mirror image comparison of the polarization angle profile of the emission intensity and thus can scale the breaking of symmetry in a convenient way.

The method is applicable in detecting emergence of chiral structure of opaque samples such as minerals. Even mineral samples in a small amount can be studied, without knowing the crystal structure at a miniaturized scale. For example, in some embodiments, less than 100 mg, less than 10, mg, or less that 1 mg, e.g., 1-10 mg of sample (e.g., dry solid or powdered sample) may be used.

The output chirality vector can serve as a substance signature (which can serve as classifier of different chiral substances).

Additional Exemplary Applications

Chiral mineral surfaces may play a significant role in local selection and concentration of chiral molecules. The possible emergence of chirality of biomolecules from chiral crystalline samples, e.g., calcite crystal showing differential affinity for L- and D-amino acids, may also have important astrophysical implications. Previously, it has been difficult to determine the chirality of opaque substances such like minerals, and in most cases a solution phase study with some degree of transparency remains the only option (other than material-specific techniques such as magnetic circular dichroism). Techniques described herein may be applied to measure the chirality of such surfaces.

The chirality of nano-crystalline objects has also been of extensive studies. While the chiral symmetry breaking during crystallization is known, enantiomeric selection could only being studied while re-dissolving the crystal in solution phase. The techniques disclosed herein bypass the transparency requirement of the test sample, and so may be used to measure chirality of nano-crystalline objects.

Although a number of exemplary applications of techniques described herein have been presented, it is to be understood that these examples are nonlimiting. The techniques described herein may be applied to any suitable application.

It is noted that embodiments disclosed herein are not just an alternative method of finding the fluorescence anisotropy of a substance (which need not to be directly related to chiral behavior). The polarization angular variation provides much richer information than the conventional anisotropy value. As shown above the polarization angle dependent anisotropy can be found, and a triad (or more) of anisotropy measurements (at three angles) can be used to formulate a chiral vector which provides rich information about the properties of the substance under test. Thus, embodiments disclosed herein are not incremental additions to existing techniques but provide independent methods to determine chirality and material identification, of both transparent and opaque system.

EXAMPLES

General Methods Used in Examples 1-6

In each of Examples 1-6, the chirality of various samples was measured using the procedures for measuring chirality described above. Fluorescence data was collected using a Quantamaster 40 spectrothiorometer, available from Photon Technology International (PTI) of 300 Birmingham Road, Birmingham, N.J.

The Quantamaster 40 spectrofluorometer includes a high efficiency continuous Xenon arc lamp coupled with Czerny-Turner monochromator to provide substantially monochromatic excitation light at wavelengths ranging from 185 nm to 900 urn. The system includes and photon counting detector coupled with a second Czerny-Turner monochromator for detecting fluorescent emission from the sample at a selected emission wavelength.

Felix 32 control software, also available from PTI, was used to control the polarization of the excitation and emission light, as detailed above. The control software was programmed in such a way that for each excitation polarization angle (corresponding to the angle of the excitation side polarizer 110 shown in FIG. 1), the measured emission polarization angle (corresponding to the angle of the emission side polarizer 130 shown in FIG. 1) was varied from 0-360 degrees at an interval of 45 degrees. Emission photon count measurements were obtained at the various polarization angle configurations as saved and a data set spreadsheet file. In each case the measurement was carried out at room temperature, with a liquid sample solution.

In Examples 1-6 below, when an amino acid (e.g., tryptophan, tyrosine, or phenylalanine) was tested, an aqueous stock solution of amino acids was prepared at a concentration of 10 µM under slightly alkaline condition. This stock solution was then diluted to form a final test solution with an amino acid concentration of 125 µM.

When pyrene was tested, a solution of pyrene in toluene was prepared at a concentration of concentration 10 mM. This stock solution was then diluted with additional toluene to form a final test solution with a pyrene concentration of 125 µM.

The excitation light wavelength and the measured emission wavelength were chosen based on the fluorescence characteristics of the sample under test. The selected wavelength values are detailed in Table 1, below.

TABLE 1

| Sample | Excitation Wavelength | Emission Wavelength |
|---|---|---|
| Tryptophan | 280 nm | 350 nm |
| Tyrosine | 274 nm | 302 nm |
| Pyrene | 334 nm | 394 nm |
| Phenylalanine | 257 nm | 282 nm |

The intensity of the measured emission varied as a function of polarization angle, in the range of $10^{-3}$ counts/second to $2 \times 10^5$ counts/second.

Each data set was stored in a spreadsheet file which was then analyzed using the MATLAB technical computing environment (available from MathWorks of 3 Apple Hill Drive, Natick Mass.). The results of the analysis are detailed in Examples 1-6 below.

Example 1

Analysis of Chiral Molecules D-Tyr and L-Tyr by Varying Polarization Angles

Figure 2A:
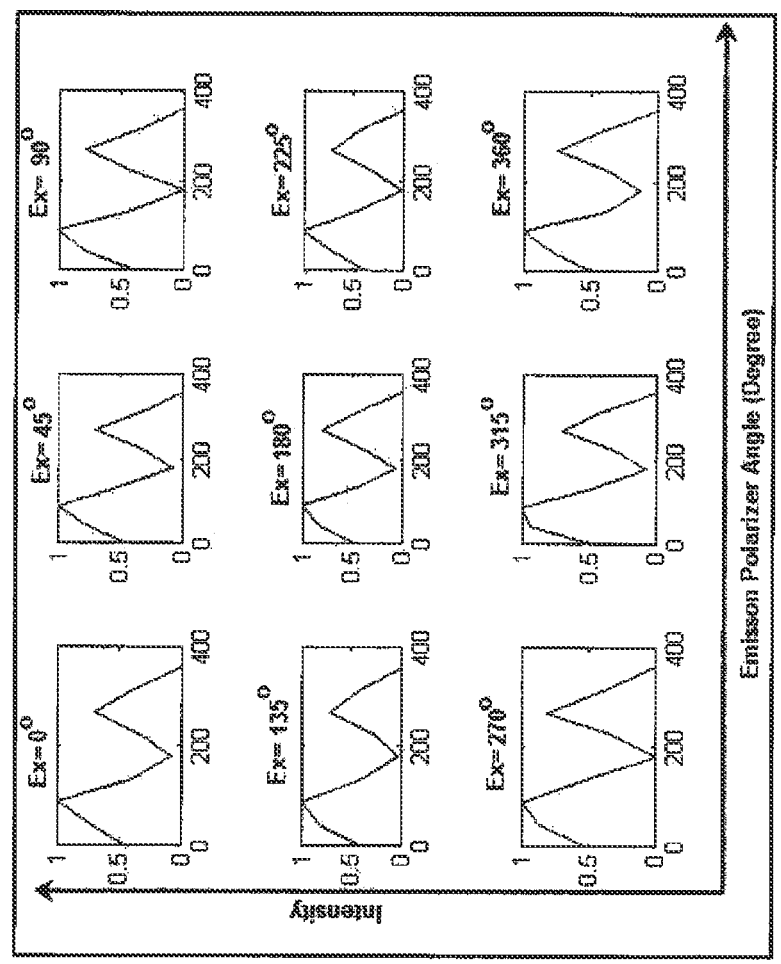
Figure 2B:
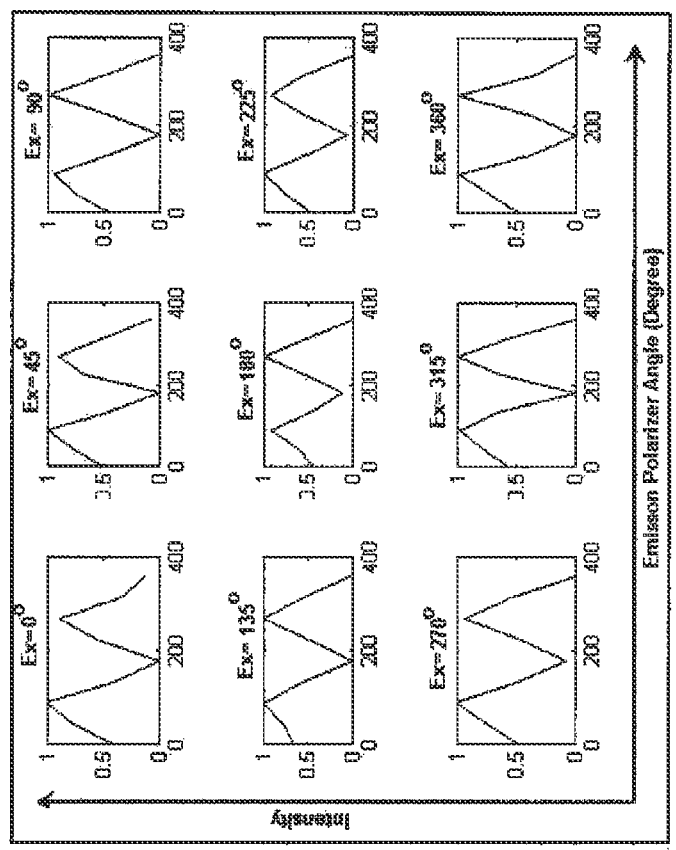

FIGS. 2A and 2B are plots showing polarization angle variation of the fluorescent intensity pattern for the chiral molecule tyrosine. The FIGS. 2A and 2B are for D and L tyrosine respectively. The water Raman line was corrected for each samples measured. That is, as the samples were dissolved in distilled water, the contribution of scattering intensities at the emission wavelength for a particular excitation wavelength was corrected by taking only distilled water (without any amino acid) in the sample holder 116 and measured in the system 100 using the sample experimental parameters. As there was no such fluorescence of water at the excitation window of the amino acid (e.g., tryptophan, tyrosine, or phenylalanine), the intensities at the emission windows are considered due to scattering which is designated as Raman scattering from the Raman line of water. This background scattering was then corrected for in the measurement of the sample.

Note that the intensity patterns shown in FIGS. 2A and 2B are asymmetric, characteristic of the chiral nature of the molecule.

Example 2

Analysis of Pyrene: An Achiral Molecule

Figure 3:
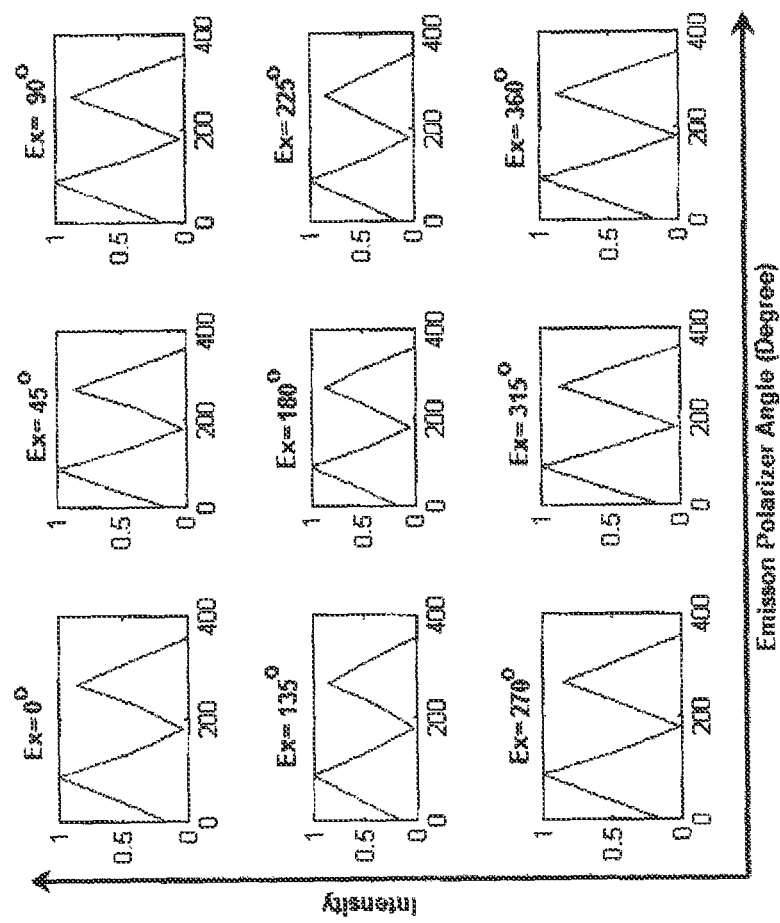
FIG. 3 is a plot showing the highly-symmetric intensity pattern for an achiral molecule pyrene.

FIG. 3 is a plot showing the intensity pattern for the achiral molecule pyrene. Unlike the patterns measured in the analysis of chiral molecules in Example 1 (shown in FIG. 2A and FIG. 2B), the patterns found for the achiral pyrene molecule (shown in FIG. 3) are highly symmetric. The small differences in the pattern amplitudes are due to the polarizer alignment. The polarizer-induced offset can be further eliminated if the chirality is expressed relative to this reference achiral compound (achiral, but fluorescent). It may be noted that the extent of the observed asymmetry is much lower, indicating that there is only a small offset value resulting from the experimental setup including the polarizer.

Example 3

Analysis of Chiral Molecules D-Trp and L-Trp

In one embodiment, additional information can be extracted from the method described herein. For example, a characteristic spectroscopic signature of a sample (e.g., fluorophore) can be obtained using the differential profile. In other words, the degree of symmetry breaking for a given molecule depends on the nature of the molecule. Thus, different molecules can be discriminated from the differential signals. The differences can be obtained between the emission intensities of the enantiomeric molecule and its mirror image.

In the example shown in FIG. 5A, the asymmetric factors for the tryptophan molecule (D-Trp and L-Trp) are plotted against the emission-side polarizer angles. The differential anisotropy between two arms of the observed "M"-like pattern can be shown by dividing them into two halves, and then comparing the reflected image (mirror set at mid point—180°) perpendicular to the x-axis. As illustrated, the plots for D-Trp and L-Trp are significantly different, allowing for clear identification between the two stereoisomers.

Example 4

Analysis of Chiral Molecules D-Phe and L-Phe

The asymmetric factors of chiral molecules phenyl alanine (D-Phe and L-Phe) obtained using the methods and systems described above are plotted in FIG. 5B. As in the previous example, each stereoisomer can be clearly distinguished from the other.

Moreover, as described herein, the asymmetric factors can be used to construct a chiral vector which may be used to identify not only the chirality of the sample, but also the type of molecule, as described below in Example 6.

Example 5

Analysis of Chiral Molecules D-Tyr and L-Tyr

The asymmetric factors of chiral molecules tyrosine (D-Tyr and L-Tyr) obtained using the methods and systems described above are plotted in FIG. 5C. As in the previous example, each stereoisomer can be clearly distinguished from the other.

The asymmetric factors can be used to construct a chiral vector, which is compared with those of the tryptophan and the phenylalanine molecules, as described below in Example 6.

Example 6

Comparison of Chiral Vectors of D-Trp, L-Trp, D-Phe, L-Phe, L-Tyr

In one embodiment, to substantiate the chiral signature of a given molecule, a chiral vector is provided. FIG. 6 demonstrates the variation of the chiral vectors for the respective amino acids D-Trp, L-Trp, D-Phe, L-Phe, D-Tyr, and L-Tyr. The three components of the chiral vector represent the asymmetry at three different emission polarization angles (0°, 45°, and 90° respectively). The D and L types are shown by similar line type. The X, Y and Z are dimensionless quantities normalized by a typical achiral fluorescent molecule pyrene (e.g., derived from FIG. 3). The angles 0°, 45°, and 90° are chosen as an example, and other selections of the angles can also be used. For example, any angles from 0° to 360° that are multiples of OP, 45°, and 90° can be used.

In various embodiments, angles other than multiples of 45 degrees may be chosen, e.g., multiples of 30 degrees. In some embodiments 45 degree interval is used to minimize the time for data collection and to provide a simple basis for construction of the chirality vector.

The chiral vector not only indicates whether molecule is chiral, it can also scale the chirality of different chiral molecules depending on the magnitude of this vector. A new signature principle is thus obtained. Thus, the method not only can distinguish between L-Trp and D-Trp, but also can distinguish between L-Trp and L-Phe (as the chiral vectors will be different in each case).

Example 7

Analysis of Nonfluorescent Chiral Molecules ATP and L-ATP with Fluorescent Tag

In each of Examples 1-6, above, the substance under test naturally exhibited fluorescence. In the current example, the chirality of a non-fluorescent molecule is tested by tagging the molecule with a non-chiral, fluorescent substance.

In the current example, two samples are prepared. The first test sample is made up of adenosine triphosphate (ATP). The second test sample is made up of the enantiomer of adenosine triphosphate (L-ATP). For each sample, the ATP or L-ATP molecules are labeled with a non-chiral pyrene fluorophore, e.g., by coupling the pyrene using a butyryl linker to the ribose moiety of the ATP or L-ATP as described in Hiratsuka, Biophysical Journal, Vol. 72 pp. 843-849 (1997).

The pyrene tagged samples are then analyzed using techniques and substantially similar to those described with reference to Examples 1-6 to measure the asymmetric factors of each of the samples, and to generate a chirality vector for each sample. The resulting vectors may be compared, as described above, to clearly distinguish the ATP sample from the L-ATP sample.

Example 8

Chiral Metallic Nanoclusters Grown on DNA

As described in G. Shemer, et al., Chirality of Silver Nanoparticles Synthesized on DNA J. Am. Chem. Soc., 2006, 128 (34), pp 11006-11007, silver nanocrystals grown on DNA, e.g. a poly(dG)-poly(dC) double stranded DNA scaffold, may display circular dichroism at their surface plasmon excitation band. This chiral plasmon signature is not observed in control experiment where silver nanocrystals of similar size were produced without the DNA template and adsorbed to the DNA. It is concluded that the DNA templated Ag nanocrystals had a preferred structural handedness.

Systems and methods of the described herein may be used applied to samples measure the chirality of such substances. For example, in some embodiments, the presence of DNA may be detected by growing metallic nanoclusters using the DNA as a template molecule, and then detecting the chirality of resulting structure using the systems and methods described herein.

Example 9

Analysis of Chiral Solid Materials

As described above, the techniques described herein may be used to measure the chiral properties of solid or opaque materials. For example calcite is a carbonate mineral and the most stable polymorph of calcium carbonate ($CaCO_3$). Single calcite crystals may form in one of two enantiomeric states (D-calcite and L-calcite). Due to the presence of impurities calcite crystals typically fluoresce to emit light in the visible spectrum in response to excitation in the UV spectrum.

In this example, two samples are prepared. The first sample is a thin layer of D-calcite formed on the surface of a first slide. The second sample is a thin layer of L-calcite formed on the surface of a second slide.

Each sample is analyzed using a system of the type shown in FIG. 1. For each sample, the slide is placed in sample holder 116 of system 100 for measuring chiral properties of a sample. The system 100 includes a radiation source 102, such as a Xenon lamp, to generate an excitation radiation 104, in the UV range.

The excitation radiation 104 goes through a first, excitation-side, monochromator 106 and becomes a radiation beam 108 having a narrow spectral range. The radiation beam 108 goes through a first, excitation-side, polarizer 110, and becomes a polarized excitation beam 112. The excitation-side polarizer 110 is actuated by a first actuator (not shown) which controls the polarization angle of the excitation beam 112. The polarized excitation beam 112, of which an angular distribution of polarization can be varied, excites the sample disposed in a sample holder 116, and causes a fluorescence emission 118 in the visible portion of the spectrum from the sample 114.

An integrating sphere (not shown) is used to remove spatial anisotropies (e.g., due to optical effects caused by the sample shape) from the fluorescence emission. The fluorescence emission 118 goes from the integrating sphere through a second, emission-side, polarizer 120, and a second, emission-side monochromator 122. The emission-side polarizer 120 is actuated by a second actuator (not shown). By varying a polarization angle to thereby pass through the emission component with the specified polarization angle, the emission-side polarizer 120 can be used to determine the polarization dependence of the fluorescence emission 118. The substantially monochromatic emission 124 carrying the polarization information is detected by a detector 126. The detected signal is analyzed by a computer 128.

The results of the measurements described above are then analyzed using conditions and techniques substantially similar to those described in Examples 1-6 to measure the asymmetric factors of each of the samples, and to generate a chirality vector for each sample. The resulting vectors may be compared, as described above, to clearly distinguish the D-calcite sample from the L-calcite sample.

Note that although a thin layer of a crystalline solid sample was used in this example, in various embodiments other forms of solid sample may be used. For example, in some embodiments, a non-crystalline solid sample may be crushed and formed into a pellet for analysis. See, e.g., Castiglioni et al., Chirality, Volume 12, pages 291-294 (2000). In various embodiments, any sample preparation techniques known in the art may be used, e.g., those described in Castiglioni et al., Chirality, Volume 12, pages 291-294 (2000) and Sparks, et al., Journal of Quantitative Spectroscopy & Radiative Transfer Volume 110, pages 1771-1779 (2009).

In some embodiments, a non-fluorescent solid sample may be tagged with an achiral fluorescent tag (e.g., of the type described in Example 7 above) and then analyzed using the techniques described herein.

As used herein the term "light" and related terms (e.g. "optical") are to be understood to include electromagnetic radiation both within and outside of the visible spectrum, including, for example, ultraviolet and infrared radiation. Portions of the electromagnetic spectrum referred to herein include are defined as followed: ultraviolet "UV" (wavelengths of 10-400 nm), visible (wavelengths of 380-760 nm), near infrared (wavelengths of 750-2500 nm), infrared (wavelengths of 750-1 mm).

As used herein, the term opaque refers to a material which does not easily transmit incident light in a given wavelength range. In some embodiments, an opaque materials transmits less than 50%, less than 40%, less than 30%, less than 20%, less than 10%, less than 1%, or even no or substantially no incident light in the given wavelength range. In some embodiments, the given wavelength range may be the ultraviolet "UV" (wavelengths of 10-400 nm), visible (wavelengths of 380-760 nm), near infrared (wavelengths of 750-2500 nm), infrared (wavelengths of 750-1 mm), or combinations, or sub-ranges thereof.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e bodies of the appended claims) are generally intended as "open" terms (e.g., the term "including" should be interpreted as "including but not limited to," the term "having" should be interpreted as "having at least," the term "includes" should be interpreted as "includes hut is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system comprising:
   a sample holder configured to hold a sample;
   a radiation source configured to emit an excitation beam for causing a fluorescent emission of the sample;
   a first polarizer disposed between the radiation source and the sample holder and configured to control a polarization angle of the excitation beam;
   a detector configured to measure an intensity of the fluorescent emission;
   a second polarizer disposed between the sample holder and the detector and configured to control a polarization angle of the fluorescent emission; and
   a computer comprising a non-transitory computer-readable storage medium having computer-readable instructions stored thereon, the computer-readable instructions being executable by a processor of the computer, to cause the computer to derive a chiral property of the sample based on the measured intensity of the fluorescent emission,
   wherein the computer is further configured to calculate an extended anisotropic expression $A(\theta)$ defined as:

$$A(\theta)=(I_{\theta,\theta}-I_{\theta,\theta+90°})/(I_{\theta,\theta}+2I_{\theta,\theta+90°})$$

wherein I is the intensity of the fluorescent emission measured at an excitation polarization angle $\theta$ (first subscript of I) and an emission polarization angle $\theta$ or $\theta+90°$ (second subscript of I),
   wherein the computer is further configured to calculate a chirality vector from the fluorescent emission based on the extended anisotropic expression,
   wherein the computer is further configured to obtain the chirality vector by obtaining asymmetric factors at a plurality of different fluorescent emission polarization angles.

2. The system of claim 1, wherein the plurality of different fluorescent emission polarization angles includes three angles.

3. The system of claim 2, wherein the computer is further configured to obtain the asymmetric factors by:
   for chiral fluorescent molecules:
      obtaining an extended anisotropy (X) at different excitation and emission polarizer angles; and
      obtaining a reciprocal of the extended anisotropy (X') at different excitation and emission polarizer angles;
   for achiral fluorescent molecules:
      obtaining an extended anisotropy (Y) at different excitation and emission polarizer angles; and
      obtaining a reciprocal of the extended anisotropy (Y') at different excitation and emission polarizer angles; and
   calculating the asymmetric factor (X−X')/(Y−Y').

4. The system of claim 1, wherein the computer is further configured to distinguish different types of molecules from the sample based on a magnitude of the chirality vector.

5. The system of claim 1, wherein the computer is further configured to derive the chiral property based on an angle of the chirality vector.

6. The system of claim 1, further comprising:
   a first monochromator disposed between the radiation source and the first polarizer, wherein the first monochromator is configured to produce a first monochromatic excitation beam; and
   a second monochromator disposed between the second polarizer and the detector, wherein the second monochromator is configured to produce a second monochromatic emission beam.

7. The system of claim 6, wherein the first monochromator is configured to transform excitation radiation to a radiation beam.

8. The system of claim 1, further comprising:
   a first actuator configured to actuate the first polarizer and control the polarization angle of the excitation beam; and
   a second actuator configured to actuate the second polarizer and control the polarization angle of the fluorescent emission.

9. The system of claim 1, further comprising an achiral fluorescent tag coupled to the sample.

10. The system of claim 9, wherein the achiral fluorescent tag includes one of pyrene or biphenyl-4-carboxylic acid.

11. The system of claim 1, further comprising a device configured to separate a compound in a desired chirality from the sample based on the detected chirality properties of the sample.

12. The system of claim 1, further comprising an integrating sphere configured to measure a fluorescence emission from the sample.

13. The system of claim 1, wherein the sample is at least one of a solid, a liquid suspension, a semi-solid, a powder, a crystalline, or a film form.

14. The system of claim 1, wherein the radiation source comprises at least one of a laser diode, an X-Ray source, or a particle beam.

15. An apparatus comprising:
   a sample holder configured to hold a sample;
   a radiation source configured to emit an excitation beam for causing a fluorescent emission of the sample;
   a first polarizer disposed between the radiation source and the sample holder and configured to control a polarization angle of the excitation beam;
   a detector configured to detect the fluorescent emission indicative of a chiral property of the sample; and
   a computer comprising a non-transitory computer-readable storage medium having computer-readable instructions stored thereon, the computer-readable instructions being executable by a processor of the computer, to cause the computer to derive a chiral property of the sample based on the measured intensity of the fluorescent emission,
   wherein the computer is further configured to calculate an extended anisotropic expression $A(\theta)$ defined as:

$$A(\theta)=(I_{\theta,\theta}-I_{\theta,\theta+90°})/(I_{\theta,\theta}+2I_{\theta,\theta+90°})$$

wherein I is the intensity of the fluorescent emission measured at an excitation polarization angle $\theta$ (first subscript of I) and an emission polarization angle $\theta$ or $\theta+90°$ (second subscript of I),
   wherein the computer is further configured to calculate a chirality vector from the fluorescent emission based on the extended anisotropic expression,
   wherein the computer is further configured to obtain the chirality vector by obtaining asymmetric factors at a plurality of different fluorescent emission polarization angles.

16. The apparatus of claim 15, further comprising a second polarizer disposed between the sample holder and the detector and configured to determine a polarization dependence of the fluorescent emission.

17. A non-transitory computer-readable storage medium having computer-readable instructions stored thereon, the instructions being executable by a processor of a computing system, wherein the instructions comprise:

instructions to derive a chiral property of a sample from a fluorescent emission of the sample;

instructions to calculate to an extended anisotropic expression $A(\theta)$ defined as:

$$A(\theta) = \frac{I_{\theta,\theta} - I_{\theta,\theta+90°}}{I_{\theta,\theta} + 2I_{\theta,\theta+90°}}$$

wherein I is the intensity of the fluorescent emission measured at an excitation polarization angle $\theta$ (first subscript of I) and an emission polarization angle $\theta$ or $\theta+90°$ (second subscript of I);

instructions to calculate a chirality vector from the fluorescent emission based on the extended anisotropic expression;

instructions to obtain the chirality vector by obtaining asymmetric factors at a plurality of different fluorescent emission polarization angles; and instructions to distinguish different types of molecules from the sample based on a magnitude of the chirality vector.

\* \* \* \* \*

UNITED STATES PATENT AND TRADEMARK OFFICE
CERTIFICATE OF CORRECTION

| | | |
|---|---|---|
| PATENT NO. | : 8,982,344 B2 | |
| APPLICATION NO. | : 14/134899 | |
| DATED | : March 17, 2015 | |
| INVENTOR(S) | : Anjan Kr. Dasgupta et al. | |

It is certified that error appears in the above-identified patent and that said Letters Patent is hereby corrected as shown below:

In the Drawings

In Fig. 2A, Sheet 2 of 11, delete "Emisson" and insert -- Emission --, therefor.

In Fig. 2B, Sheet 3 of 11, delete "Emisson" and insert -- Emission --, therefor.

In Fig. 3, Sheet 4 of 11, delete "Emisson" and insert -- Emission --, therefor.

In Fig. 5A, Sheet 6 of 11, delete "Emisson" and insert -- Emission --, therefor.

In Fig. 5B, Sheet 7 of 11, delete "Emisson" and insert -- Emission --, therefor.

In Fig. 5C, Sheet 8 of 11, delete "Emisson" and insert -- Emission --, therefor.

In the Specification

In Column 1, Line 7, delete "divisional of" and insert -- divisional under 35 U.S.C. §121 of --, therefor.

In Column 1, Line 9, delete "stage of" and insert -- stage filing under 35 U.S.C. §371 of --, therefor.

In Column 1, Line 10, delete "Jun. 21, 2011," and insert -- Jun. 21, 2011, now Pat. No. 8,638,434, --, therefor.

In Column 2, Line 10, delete "nanotechnologics" and insert -- nanotechnologies --, therefor.

In Column 4, Line 54, delete "nonmaterial" and insert -- nanomaterial --, therefor.

Signed and Sealed this
Twenty-eighth Day of July, 2015

Michelle K. Lee
*Director of the United States Patent and Trademark Office*

CERTIFICATE OF CORRECTION (continued)
U.S. Pat. No. 8,982,344 B2

In Column 7, Line 6, delete "FIG. 213" and insert -- FIG. 2B --, therefor.

In Column 8, Line 1, delete "chirality" and insert -- chirality in --, therefor.

In Column 8, Line 2, delete "oldies." and insert -- studies. --, therefor.

In Column 8, Line 7, delete "rock-Re" and insert -- rock-like --, therefor.

In Column 9, Line 6, delete "samples, in" and insert -- samples. In --, therefor.

In Column 9, Line 18, delete "chirooptical" and insert -- chiroptical --, therefor.

In Column 9, Line 51, delete "For achiral" and insert -- For an achiral --, therefor.

In Column 10, Line 6, delete "samples cm" and insert -- samples can --, therefor.

In Column 11, Line 11, delete "(20°, 60 °, 80 °," and insert -- (20°, 40 °, 60 °, 80 °, --, therefor.

In Column 13, Line 21, delete "based on" and insert -- based on a --, therefor.

In Column 13, Line 33, delete "($\theta_g$)" and insert -- ($\theta_\varepsilon$) --, therefor.

In Column 14, Line 25, delete "charming" and insert -- changing --, therefor.

In Column 15, Line 17, delete "angles, in" and insert -- angles. In --, therefor.

In Column 16, Line 51, delete "900 urn." and insert -- 900 nm. --, therefor.

In Column 17, Line 8, delete "10mM." and insert -- 10μM. --, therefor.

In Column 18, Line 37, delete "phenyl alanine" and insert -- phenylalanine --, therefor.

In Column 19, Line 11, delete "OP, 45°," and insert -- 0 ° , 45°, --, therefor.

In Column 19, Line 27, delete "Nonfluorescent" and insert -- Non-fluorescent --, therefor.

In Column 21, Line 53, delete "(e" and insert -- (e.g., --, therefor.

In Column 21, Line 58, delete "hut" and insert -- but --, therefor.

In Column 22, Line 23, delete "A, B, C," and insert -- A, B, and C, --, therefor.